United States Patent [19]
Ficht et al.

[11] Patent Number: 5,348,857
[45] Date of Patent: Sep. 20, 1994

[54] PROBES AND METHOD FOR IDENTIFYING SPECIES AND BIOVARS OF BRUCELLA

[75] Inventors: Thomas A. Ficht; L. Garry Adams, both of College Station, Tex.

[73] Assignee: Texas A & M University, College Station, Tex.

[21] Appl. No.: 972,791

[22] Filed: Nov. 6, 1992

Related U.S. Application Data

[63] Continuation-in-part of Ser. No. 527,017, May 22, 1990.

[51] Int. Cl.5 .............................................. C12P 19/34
[52] U.S. Cl. ........................................ 435/6; 435/91.2; 435/29; 435/34; 436/501; 436/811; 536/23.7; 935/77; 935/78
[58] Field of Search .................... 435/6, 9, 1.2, 29, 34; 436/501, 811; 536/23.7; 935/77, 78

[56] References Cited

U.S. PATENT DOCUMENTS

| | | | |
|---|---|---|---|
| 4,358,535 | 3/1982 | Falkow et al. | 435/5 |
| 4,683,202 | 7/1987 | Mullis | 435/91 |

OTHER PUBLICATIONS

Nicoletti, *Am. J. Vet. Res.*, (1981) 42:1494–1497.
Farrell, *Res. Vet. Sci.*, (1974) 16:280–286.
Ficht et al., *Mol. Microbiol.*, (1990) 4:1135–1142.
Ficht et al., *Infect. Immunol.*, (1988) 56:2036–2046.
Heck et al., *Am. J. Vet. Res.*, (1980) 41:2082–2084.
Huber et al., *Am. J. Vet. Res.*, (1986) 47:1529–1531.
Saiki et al., *Science*, (1988) 239:487–491.
Timbs et al., *N.Z. vet. J.*, (1978) 26:52–56.
Embase Abstract No. 89259898, Ficht et al., *Infect. Immun.* (USA), 1989, (3281–3291).
Hudson et al., *J. Miol. Bio.*, (1984) 180:1023–1051.
Raitio et al., *The EMBO Journal*, 6:2825–2833 (1987).

*Primary Examiner*—Amelia Burgess Yarbrough
*Attorney, Agent, or Firm*—Pravel, Hewitt, Kimball & Krieger

[57] ABSTRACT

A method for detecting Brucella infection in an animal which is reliable, rapid, and able to identify species and biovars of Brucella. The detection method includes the amplification of the omp2 gene locus of Brucella and analysis of restriction digestion fragments specific to Brucella and to individual species and groups of biovars of Brucella.

13 Claims, 26 Drawing Sheets

FIG. 2 A

SPECIES ALIGNMENT FORMATTED ALIGNMENT

```
CONCENSUS            CAGGCGATCT TCCGCGACCC CTGTAGAAAG ACTGCGGTCA GCATAAAAAG CAAGCATCTG   60

B.OVIS 1ST OMP II    .......... .......... .......... .......... .......... ..........   60
B.SUIS OMP II        .......... .......... .......... .......... .......... ..........   60
B.B5 OMP II          .......... .......... .......... .......... .......... ..........   60
B.MELIT 1ST OMP II   .......... .......... .......... .......... .......... ..........   59
B.CANIS OMP II       .......... .......... .......... .......... .......... ..........   60
B.NEOTOMAE OMP II    .......... .......... .......... .......... .......... ..........   60
B.2308 OMP II        .......... .......... .......... .......... .......... ..........   60

CONCENSUS            ATGCTGCACG AGGGCAACAA AAAACCCGGY ATTTCTGCCG GGTTTCTGTA TCCAATCCGT  120

B.OVIS 1ST OMP II    .......... .......... .........C .......... .......... ..........  120
B.SUIS OMP II        .......... .......... .........T .......... .......... ..........  120
B.B5 OMP II          .......... .......... .........C .......... .......... ..........  120
B.MELIT 1ST OMP II   .......... .......... .........C .......... .......... ..........  119
B.CANIS OMP II       .......... .......... .........T .......... .......... ..........  120
B.NEOTOMAE OMP II    .......... .......... .........C .......... .......... ..........  120
B.2308 OMP II        .......... .......... .........C .......... .......... ..........  120

CONCENSUS            AATGGATTAG AACGAACGCT GGAAGCGAAC GATACCGCCC CAAGCATTGT CTTCAGCAAC  180

B.OVIS 1ST OMP II    .......... .......... .......... .......... .......... ..........  180
B.SUIS OMP II        .......... .......... .......... .......... .......... ..........  180
B.B5 OMP II          .......... .......... .......... .......... .......... ..........  180
B.MELIT 1ST OMP II   .......... .......... .......... .......... .......... ..........  179
B.CANIS OMP II       .......... .......... .......... .......... .......... ..........  180
B.NEOTOMAE OMP II    .......... .......... .......... .......... .......... ..........  180
B.2308 OMP II        .......... .......... .......... .......... .......... ..........  180

CONCENSUS            RGTGTTCTTC CACTCGCCAC CAAACTTGGT GTAGGAAACT TCCGGMGYAA CGGTGAAGCC  240

B.OVIS 1ST OMP II    G......... .......... .......... .......... .....C.T.. ..........  240
B.SUIS OMP II        G......... .......... .......... .......... .....C.T.. ..........  240
B.B5 OMP II          G......... .......... .......... .......... .....C.T.. ..........  240
B.MELIT 1ST OMP II   A......... .......... .......... .......... .....C.T.. ..........  239
B.CANIS OMP II       G......... .......... .......... .......... .....C.T.. ..........  240
B.NEOTOMAE OMP II    G......... .......... .......... .......... .....A.C.. ..........  240
B.2308 OMP II        G......... .......... .......... .......... .....C.T.. ..........  240
```

FIG. 2 A

```
CONCENSUS             AGGAACCAGT TCGTAAGCAA CGTTAGCCGT AACTGCCGTC TTGCCCCAGT CGTCATGCGC  300

B.OVIS 1ST OMP II     .......... .......... .......... .......... .......... ..........  300
B.SUIS OMP II         .......... .......... .......... .......... .......... ..........  300
B.B5 OMP II           .......... .......... .......... .......... .......... ..........  300
B.MELIT 1ST OMP II    .......... .......... .......... .......... .......... ..........  299
B.CANIS OMP II        .......... .......... .......... .......... .......... ..........  300
B.NEOTOMAE OMP II     .......... .......... .......... .......... .......... ..........  300
B.2308 OMP II         .......... .......... .......... .......... .......... ..........  300

CONCENSUS             AGCCTGCAGR TTGAAGGYWG CCTTYTSSGT RGCMWKRWAC TTYRSACCAC CCCAGACAGC  360

B.OVIS 1ST OMP II     .........G .......CA. ....C.GC.. A..CTGAT.. ..CAG..... ..........  360
B.SUIS OMP II         .........G .......CA. ....C.GC.. A..CTGAT.. ..CAG..... ..........  360
B.B5 OMP II           .........G .......CA. ....C.GC.. A..CTGAT.. ..CAG..... ..........  360
B.MELIT 1ST OMP II    .........G .......CA. ....C.GC.. A..CTGAT.. ..CAG..... ..........  359
B.CANIS OMP II        .........G .......CA. ....C.GC.. A..CTGAT.. ..CAG..... ..........  360
B.NEOTOMAE OMP II     .........A .......TT. ....T.CG.. G..AATGA.. ..TGC..... ..........  360
B.2308 OMP II         .........G .......CA. ....C.GC.. A..CTGAT.. ..CAG..... ..........  360

CONCENSUS             CCAATCGCCG CCCCACTGRC CGTAGTTCTG RTYCGGCGTM GCWGCGGACG AATATGCGCC  420

B.OVIS 1ST OMP II     .......... ........A. .......... G.T......C ..T....... ..........  420
B.SUIS OMP II         .......... ........G. .......... A.C......A ..A....... ..........  420
B.B5 OMP II           .......... ........G. .......... A.C......A ..A....... ..........  420
B.MELIT 1ST OMP II    .......... ........G. .......... A.C......A ..A....... ..........  419
B.CANIS OMP II        .......... ........G. .......... A.C......A ..A....... ..........  420
B.NEOTOMAE OMP II     .......... ........A. .......... G.T......C ..T....... ..........  420
B.2308 OMP II         .......... ........G. .......... A.C......A ..A....... ..........  420

CONCENSUS             CTGCARCCAW ACCGAGAACY GGTCGGTGAT GTTGACGTCG CCACGAACCT TKGYAGCCCA  480

B.OVIS 1ST OMP II     .....G...T .........C .......... .......... .......... .T.T......  480
B.SUIS OMP II         .....A...A .........T .......... .......... .......... .G.C......  480
B.B5 OMP II           .....A...A .........T .......... .......... .......... .G.C......  480
B.MELIT 1ST OMP II    .....A...A .........T .......... .......... .......... .G.C......  479
B.CANIS OMP II        .....A...A .........T .......... .......... .......... .G.C......  480
B.NEOTOMAE OMP II     .....A...A .........T .......... .......... .......... .G.C......  480
B.2308 OMP II         .....A...A .........T .......... .......... .......... .G.C......  480
```

FIG. 2 B

```
CONCENSUS               TTCTTCKATG ACCGAGTCAT AGGCAACAAC ACCAGCGATC GAACCCCAGC CGCCAGCATA  540

B.OVIS 1ST OMP II       ......G... .......... .......... .......... .......... ..........  540
B.SUIS OMP II           ......G... .......... .......... .......... .......... ..........  540
B.B5 OMP II             ......G... .......... .......... .......... .......... ..........  540
B.MELIT 1ST OMP II      ......G... .......... .......... .......... .......... ..........  539
B.CANIS OMP II          ......G... .......... .......... .......... .......... ..........  540
B.NEOTOMAE OMP II       ......G... .......... .......... .......... .......... ..........  540
B.2308 OMP II           ......T... .......... .......... .......... .......... ..........  540

CONSENSUS               YTTCAGGCCG CCAACAACGT SMGGCATGTA RCCGTCGATS BKGTARTYGG TCGTGCCAGT  600

B.OVIS 1ST OMP II       T......... .......... GC........ A........C GT...A.C.- ----------  589
B.SUIS OMP II           C......... .......... CA........ G........G CG...G.T.. ..........  600
B.B5 OMP II             C......... .......... CA........ G........G TG...G.T.. ..........  600
B.MELIT 1ST OMP II      C......... .......... CA........ G........G TG...G.T.. ..........  599
B.CANIS OMP II          C......... .......... CA........ G........G TG...G.T.. ..........  600
B.NEOTOMAE OMP II       C......... .......... CA........ G........G TG...G.T.. ..........  600
B.2308 OMP II           C......... .......... CA........ G........G TG...G.T.. ..........  600

CONSENSUS               GTAAYYRYCR WCGTYKTCGC CACCCTGTTC GAGAGCGATC ACAGCCGAGA AGCCGTTTCC  660

B.OVIS 1ST OMP II       ----TTGT.A A...CT.... .......... .......... .......... ..........  645
B.SUIS OMP II           ....CCAC.G T...TG.... .......... .......... .......... ..........  660
B.B5 OMP II             ....CCAC.G T...TG.... .......... .......... .......... ..........  660
B.MELIT 1ST OMP II      ....CCAC.G T...TG.... .......... .......... .......... ..........  659
B.CANIS OMP II          ....CCAC.G T...TG.... .......... .......... .......... ..........  660
B.NEOTOMAE OMP II       ....CCAC.G T...TG.... .......... .......... .......... ..........  660
B.2308 OMP II           ....CCAC.G T...TG.... .......... .......... .......... ..........  660

CONSENSUS               GCCRGTGAAG GTGTASGMGA TCTTGCCGGT GCGGTAGGAG CCAGCCGAGA TCACGTCATC  720

B.OVIS 1ST OMP II       ...G...... .....G.C.. .......... .......... .......... ..........  705
B.SUIS OMP II           ...A...... .....C.A.. .......... .......... .......... ..........  720
B.B5 OMP II             ...A...... .....C.A.. .......... .......... .......... ..........  720
B.MELIT 1ST OMP II      ...A...... .....C.A.. .......... .......... .......... ..........  719
B.CANIS OMP II          ...A...... .....C.A.. .......... .......... .......... ..........  720
B.NEOTOMAE OMP II       ...A...... .....C.A.. .......... .......... .......... ..........  720
B.2308 OMP II           ...A...... .....C.A.. .......... .......... .......... ..........  720
```

FIG. 2 C

```
CONSENSUS            GTTGATGAYA TCRCCGAGGT AACCGGTGAA GGTATGGAAT TCSGATTCRT CGATACCAAC  780

B.OVIS 1ST OMP II    ........T. ..A....... .......... .......... ..G.....G. ..........  765
B.SUIS OMP II        ........C. ..G....... .......... .......... ..C.....A. ..........  780
B.B5 OMP II          ........C. ..G....... .......... .......... ..C.....A. ..........  780
B.MELIT 1ST OMP II   ........C. ..G....... .......... .......... ..C.....A. ..........  779
B.CANIS OMP II       ........C. ..G....... .......... .......... ..C.....A. ..........  780
B.NEOTOMAE OMP II    ........C. ..G....... .......... .......... ..C.....A. ..........  780
B.2308 OMP II        ........C. ..G....... .......... .......... ..C.....A. ..........  780

CONSENSUS            SYKSARACCA CCRAGCKKGA TATAYGCRAA CTSCAKRWCG GTGCCGSTGC TTACGCTGCC  840

B.OVIS 1ST OMP II    CTTG.A.... ..A...GT.. ....T..A.. ..G..GAT.. ......G... ..........  825
B.SUIS OMP II        GCGC.G.... ..G...TG.. ....C..G.. ..C..TGA.. ......C... .---------  831
B.B5 OMP II          GCGC.G.... ..G...TG.. ....C..G.. ..C..TGA.. ......C... .---------  831
B.MELIT 1ST OMP II   GCGC.G.... ..G...TG.. ....C..G.. ..C..TGA.. ......C... .---------  830
B.CANIS OMP II       GCGC.G.... ..G...TG.. ....C..G.. ..C..TGA.. ......C... .---------  831
B.NEOTOMAE OMP II    GCGC.G.... ..G...TG.. ....C..G.. ..C..TGA.. ......C... .---------  831
B.2308 OMP II        GCGC.G.... ..G...TG.. ....C..G.. ..C..TGA.. ......C... .---------  831

CONSENSUS            ATCAGCGACA TCACGATCAT CGSTKWMATY RCCRTATTKR CCATCWWSRC SYGAATTGTT  900

B.OVIS 1ST OMP II    .......... .......... ..C.GAA..C G..G....GG .....ATGA. GT........  885
B.SUIS OMP II        ---------- ---------- -.G.TTC..T A..A....TA .....TACG. CC........  870
B.B5 OMP II          ---------- ---------- -.G.TTC..T A..A....TA .....TACG. CC........  870
B.MELIT 1ST OMP II   ---------- ---------- -.G.TTC..T A..A....TA .....TACG. CC........  869
B.CANIS OMP II       ---------- ---------- -.G.TTC..T A..A....TA .....TACG. CC........  870
B.NEOTOMAE OMP II    ---------- ---------- -.G.TTC..T A..A....TA .....TACG. CC........  870
B.2308 OMP II        ---------- ---------- -.G.TTC..T A..A....TA .....TACG. CC........  870

CONSENSUS            SSYRGYRTAG TTGAAGCGCA GYKYRGTRWA GGTSYYGAGK GTGCCGAGTT CGGTTTCCGA  960

B.OVIS 1ST OMP II    GCTG.TG... .......... .CGTA..AT. ...GCC...T .......... ..........  945
B.SUIS OMP II        CGCA.CA... .......... .TTCG..GA. ...CTT...G .......... ..........  930
B.B5 OMP II          CGCA.CA... .......... .TTCG..GA. ...CTT...G .......... ..........  930
B.MELIT 1ST OMP II   CGCA.CA... .......... .TTCG..GA. ...CTT...G .......... ..........  929
B.CANIS OMP II       CGCA.CA... .......... .TTCG..GA. ...CTT...G .......... ..........  930
B.NEOTOMAE OMP II    CGCA.CA... .......... .TTCG..GA. ...CTT...G .......... ..........  930
B.2308 OMP II        CGCA.CA... .......... .TTCG..GA. ...CTT...G .......... ..........  930
```

FIG. 2 D

```
CONSENSUS            AYYSGTGKWR AMSMKGRRKK SSAAAMSRRS SMYCTTGTCC CAGCCWTTRC GRTCSGWRCC 1020

B.OVIS 1ST OMP II    .TTC...TTG .ACAT.GAGT GC...ACGAG CAC....... .....T..A. .A..C.AG.. 1005
B.SUIS OMP II        .CCG...GAA .CGCG.AGTG CG...CGAGC GCT....... .....A..G. .G..G.TA..  990
B.B5 OMP II          .CCG...GAA .CGCG.AGTG CG...CGAGC GCT....... .....A..G. .G..G.TA..  990
B.MELIT 1ST OMP II   .CCG...GAA .CGCG.AGTG CG...CGAGC GCC....... .....A..G. .G..G.TA..  989
B.CANIS OMP II       .CCG...GAA .CGCG.AGTG CG...CGAGC GCT....... .....T..A. .A..C.AG..  990
B.NEOTOMAE OMP II    .CCG...GAA .CGCG.AGTG CG...CGAGC GCT....... .....A..G. .G..G.TA..  990
B.2308 OMP II        .CCG...GAA .CGCG.AGTG CG...CGAGC GCT....... .....A..G. .G..G.TA..  990

CONSENSUS            GGWRTAAACG TCRTCGCCGC CCTTTACGTC GTAACGGACG TARCCRYKGA YGCGCAGGCA 1080

B.OVIS 1ST OMP II    ..TA...... ..G....... .......... .......... ..G..GCT.. T......... 1065
B.SUIS OMP II        ..AG...... ..A....... .......... .......... ..A..ATG.. C......... 1050
B.B5 OMP II          ..AG...... ..A....... .......... .......... ..A..ATG.. C......... 1050
B.MELIT 1ST OMP II   ..AG...... ..A....... .......... .......... ..A..ATG.. C......... 1049
B.CANIS OMP II       ..TA...... ..G....... .......... .......... ..A..ATG.. C......... 1050
B.NEOTOMAE OMP II    ..AG...... ..A....... .......... .......... ..A..ATG.. C......... 1050
B.2308 OMP II        ..AG...... ..A....... .......... .......... ..A..ATG.. C......... 1050

CONSENSUS            GGTTTCGGTG CCCGGAATGT AGAAGTAGCC AGCGCCRTAA GCGTCGCAAA CGCGGACATA 1140

B.OVIS 1ST OMP II    .......... .......... .......... ......A... .......... .......... 1125
B.SUIS OMP II        .......... .......... .......... ......G... .......... .......... 1110
B.B5 OMP II          .......... .......... .......... ......G... .......... .......... 1110
B.MELIT 1ST OMP II   .......... .......... .......... ......G... .......... .......... 1109
B.CANIS OMP II       .......... .......... .......... ......G... .......... .......... 1110
B.NEOTOMAE OMP II    .......... .......... .......... ......G... .......... .......... 1110
B.2308 OMP II        .......... .......... .......... ......G... .......... .......... 1110

CONSENSUS            TTCAACGGCT TCGGGCTCTG GCGCGACGAT TGCGTCGGCA GCYTGAGCGC CGGAAGCTGC 1200

B.OVIS 1ST OMP II    .......... .......... .......... .......... ..T....... .......... 1185
B.SUIS OMP II        .......... .......... .......... .......... ..C....... .......... 1170
B.B5 OMP II          .......... .......... .......... .......... ..C....... .......... 1170
B.MELIT 1ST OMP II   .......... .......... .......... .......... ..C....... .......... 1170
B.CANIS OMP II       .......... .......... .......... .......... ..C....... .......... 1169
B.NEOTOMAE OMP II    .......... .......... .......... .......... ..C....... .......... 1170
B.2308 OMP II        .......... .......... .......... .......... ..C....... .......... 1170
```

FIG. 2 E

```
CONSENSUS             AACCAGAGCT GCAGCGGAGC CAAGGAGAAG GCTCTTGATG TTCATTTCTG ACCTCCAGTC  1260

B.OVIS 1ST OMP II     .......... .......... .......... .......... .......... ..........  1245
B.SUIS OMP II         .......... .......... .......... .......... .......... ..........  1230
B.B5 OMP II           .......... .......... .......... .......... .......... ..........  1230
B.MELIT 1ST OMP II    .......... .......... .......... .......... .......... ..........  1229
B.CANIS OMP II        .......... .......... .......... .......... .......... ..........  1230
B.NEOTOMAE OMP II     .......... .......... .......... .......... .......... ..........  1230
B.2308 OMP II         .......... .......... .......... .......... .......... ..........  1230

CONSENSUS             AAAGTTAAAA ATGGGTCTRG GCATTCTGAT TTGGCTGAAG GACAACCTGT CCCCATCCCC  1320

B.OVIS 1ST OMP II     .......... ........G. .......... .......... .......... ..........  1305
B.SUIS OMP II         .......... ........G. .......... .......... .......... ..........  1290
B.B5 OMP II           .......... ........G. .......... .......... .......... ..........  1290
B.MELIT 1ST OMP II    .......... ........G. .......... .......... .......... ..........  1289
B.CANIS OMP II        .......... ........G. .......... .......... .......... ..........  1290
B.NEOTOMAE OMP II     .......... ........A. .......... .......... .......... ..........  1290
B.2308 OMP II         .......... ........G. .......... .......... .......... ..........  1290

CONSENSUS             TAATTGAAAA AGTCGCCCCG AAGCGCTCCT TCTTCTGAAA GTGAAGATAC TCGCCCATTT  1380

B.OVIS 1ST OMP II     .......... .......... .......... .......... .......... ..........  1365
B.SUIS OMP II         .......... .......... .......... .......... .......... ..........  1350
B.B5 OMP II           .......... .......... .......... .......... .......... ..........  1350
B.MELIT 1ST OMP II    .......... .......... .......... .......... .......... ..........  1349
B.CANIS OMP II        .......... .......... .......... .......... .......... ..........  1350
B.NEOTOMAE OMP II     .......... .......... .......... .......... .......... ..........  1350
B.2308 OMP II         .......... .......... .......... .......... .......... ..........  1350

CONSENSUS             ATTCGTTTCA ACATCGAATA TGTTCTCACA ACCTTTAYGG TGCTGCTATG AAGGGCAGTT  1440

B.OVIS 1ST OMP II     .......... .......... .......... .......C.. .......... ..........  1425
B.SUIS OMP II         .......... .......... .......... .......C.. .......... ..........  1410
B.B5 OMP II           .......... .......... .......... .......T.. .......... ..........  1410
B.MELIT 1ST OMP II    .......... .......... .......... .......C.. .......... ..........  1409
B.CANIS OMP II        .......... .......... .......... .......C.. .......... ..........  1410
B.NEOTOMAE OMP II     .......... .......... .......... .......C.. .......... ..........  1410
B.2308 OMP II         .......... .......... .......... .......T.. .......... ..........  1410
```

FIG. 2 F

```
CONSENSUS              RTTGCWGAAA TGACACRAAA TTACCTGCTT TAGCTCGGCG GATTCATGCT TTATTAACAT  1500

B.OVIS 1ST OMP II      A....A.... ......G... .......... .......... .......... ..........  1485
B.SUIS OMP II          G....T.... ......G... .......... .......... .......... ..........  1470
B.B5 OMP II            G....A.... ......G... .......... .......... .......... ..........  1470
B.MELIT 1ST OMP II     A....A.... ......G... .......... .......... .......... ..........  1469
B.CANIS OMP II         G....T.... ......A... .......... .......... .......... ..........  1470
B.NEOTOMAE OMP II      G....A.... ......G... .......... .......... .......... ..........  1470
B.2308 OMP II          G....A.... ......G... .......... .......... .......... ..........  1470

CONSENSUS              AAGTRAACGC GAATTAACCG ATGTTAACGT TTGAAAATGC AAGTTTTTTA GGATCGCCTR  1560

B.OVIS 1ST OMP II      ....G..... .......... .......... .......... .......... .........G  1545
B.SUIS OMP II          ....G..... .......... .......... .......... .......... .........A  1530
B.B5 OMP II            ....G..... .......... .......... .......... .......... .........G  1530
B.MELIT 1ST OMP II     ....G..... .......... .......... .......... .......... .........G  1530
B.CANIS OMP II         ....A..... .......... .......... .......... .......... .........A  1529
B.NEOTOMAE OMP II      ....G..... .......... .......... .......... .......... .........G  1530
B.2308 OMP II          ....G..... .......... .......... .......... .......... .........G  1530

CONSENSUS              CMGAATAAAG CCGCRRATCT TTCGTCGAAA CAGCCCTTAA CGGAATATGT CGGCAAGGTG  1620

B.OVIS 1ST OMP II      .C........ ....GA.... .......... .......... .......... ..........  1605
B.SUIS OMP II          .C........ ....GA.... .......... .......... .......... ..........  1590
B.B5 OMP II            .A........ ....GA.... .......... .......... .......... ..........  1590
B.MELIT 1ST OMP II     .C........ ....GG.... .......... .......... .......... ..........  1589
B.CANIS OMP II         .C........ ....GA.... .......... .......... .......... ..........  1590
B.NEOTOMAE OMP II      .C........ ....AA.... .......... .......... .......... ..........  1590
B.2308 OMP II          .A........ ....GA.... .......... .......... .......... ..........  1590

CONSENSUS              GCAAGAATCG TCTGAACGGA GAGCAGAAAC CTCGAATCCG TTTCATTTAA TAAGGGCAAG  1680

B.OVIS 1ST OMP II      .......... .......... .......... .......... .......... ..........  1665
B.SUIS OMP II          .......... .......... .......... .......... .......... ..........  1650
B.B5 OMP II            .......... .......... .......... .......... .......... ..........  1650
B.MELIT 1ST OMP II     .......... .......... .......... .......... .......... ..........  1649
B.CANIS OMP II         .......... .......... .......... .......... .......... ..........  1650
B.NEOTOMAE OMP II      .......... .......... .......... .......... .......... ..........  1650
B.2308 OMP II          .......... .......... .......... .......... .......... ..........  1650
```

FIG. 2 G

| | | | | | | | |
|---|---|---|---|---|---|---|---|
| CONSENSUS | TGCGTGCCGG | TGCTAAATTG | TGGGCCTTTT | TAAGCGCGCY | ATATATATAA | AGAGAATAAT | 1740 |
| B.OVIS 1ST OMP II | .......... | .......... | .......... | .........C | .......... | .......... | 1725 |
| B.SUIS OMP II | .......... | .......... | .......... | .........T | .......... | .......... | 1710 |
| B.B5 OMP II | .......... | .......... | .......... | .........C | .......... | .......... | 1710 |
| B.MELIT 1ST OMP II | .......... | .......... | .......... | .........C | .......... | .......... | 1709 |
| B.CANIS OMP II | .......... | .......... | .......... | .........T | .......... | .......... | 1710 |
| B.NEOTOMAE OMP II | .......... | .......... | .......... | .........C | .......... | .......... | 1710 |
| B.2308 OMP II | .......... | .......... | .......... | .........C | .......... | .......... | 1710 |
| CONSENSUS | CCGCAGGAAA | TTTTACCAGT | TAATGCGTAA | ATCGCTTGAA | ATGCCCAGGC | GTACCGGTTA | 1800 |
| B.OVIS 1ST OMP II | .......... | .......... | .......... | .......... | .......... | .......... | 1785 |
| B.SUIS OMP II | .......... | .......... | .......... | .......... | .......... | .......... | 1770 |
| B.B5 OMP II | .......... | .......... | .......... | .......... | .......... | .......... | 1770 |
| B.MELIT 1ST OMP II | .......... | .......... | .......... | .......... | .......... | .......... | 1769 |
| B.CANIS OMP II | .......... | .......... | .......... | .......... | .......... | .......... | 1770 |
| B.NEOTOMAE OMP II | .......... | .......... | .......... | .......... | .......... | .......... | 1770 |
| B.2308 OMP II | .......... | .......... | .......... | .......... | .......... | .......... | 1770 |
| CONSENSUS | TCTCGCCTTT | ACCGGAGAGG | TGGCCGAGTG | GTCGAAGGCG | CTCCCCTGCT | AAGGGAGTAG | 1860 |
| B.OVIS 1ST OMP II | .......... | .......... | .......... | .......... | .......... | .......... | 1845 |
| B.SUIS OMP II | .......... | .......... | .......... | .......... | .......... | .......... | 1830 |
| B.B5 OMP II | .......... | .......... | .......... | .......... | .......... | .......... | 1830 |
| B.MELIT 1ST OMP II | .......... | .......... | .......... | .......... | .......... | .......... | 1829 |
| B.CANIS OMP II | .......... | .......... | .......... | .......... | .......... | .......... | 1830 |
| B.NEOTOMAE OMP II | .......... | .......... | .......... | .......... | .......... | .......... | 1830 |
| B.2308 OMP II | .......... | .......... | .......... | .......... | .......... | .......... | 1830 |
| CONSENSUS | ACCTCAAAAG | GGTCTCGTGG | GTTCGAATCC | CATCCTCTCC | GCCAGTTTTT | CCAATATCCC | 1920 |
| B.OVIS 1ST OMP II | .......... | .......... | .......... | .......... | .......... | .......... | 1905 |
| B.SUIS OMP II | .......... | .......... | .......... | .......... | .......... | .......... | 1890 |
| B.B5 OMP II | .......... | .......... | .......... | .......... | .......... | .......... | 1890 |
| B.MELIT 1ST OMP II | .......... | .......... | .......... | .......... | .......... | .......... | 1889 |
| B.CANIS OMP II | .......... | .......... | .......... | .......... | .......... | .......... | 1890 |
| B.NEOTOMAE OMP II | .......... | .......... | .......... | .......... | .......... | .......... | 1890 |
| B.2308 OMP II | .......... | .......... | .......... | .......... | .......... | .......... | 1890 |

FIG. 2 H

| | | | | | | | |
|---|---|---|---|---|---|---|---|
| CONSENSUS | AGCAAATCTT | TATGTGTTCG | ACGCGCTTGA | TTTCATACGG | AATCGGCTTT | TACCCCTCGC | 1980 |
| B.OVIS 1ST OMP II | .......... | .......... | .......... | .......... | .......... | .......... | 1965 |
| B.SUIS OMP II | .......... | .......... | .......... | .......... | .......... | .......... | 1950 |
| B.B5 OMP II | .......... | .......... | .......... | .......... | .......... | .......... | 1950 |
| B.MELIT 1ST OMP II | .......... | .......... | .......... | .......... | .......... | .......... | 1949 |
| B.CANIS OMP II | .......... | .......... | .......... | .......... | .......... | .......... | 1950 |
| B.NEOTOMAE OMP II | .......... | .......... | .......... | .......... | .......... | .......... | 1950 |
| B.2308 OMP II | .......... | .......... | .......... | .......... | .......... | .......... | 1950 |
| CONSENSUS | GCACTGAATC | TCTGTTTTTC | CAGGCTACGA | ATCCAGAAAA | CAAGCAAGCC | ATTGATAAGT | 2040 |
| B.OVIS 1ST OMP II | .......... | .......... | .......... | .......... | .......... | .......... | 2025 |
| B.SUIS OMP II | .......... | .......... | .......... | .......... | .......... | .......... | 2010 |
| B.B5 OMP II | .......... | .......... | .......... | .......... | .......... | .......... | 2010 |
| B.MELIT 1ST OMP II | .......... | .......... | .......... | .......... | .......... | .......... | 2009 |
| B.CANIS OMP II | .......... | .......... | .......... | .......... | .......... | .......... | 2010 |
| B.NEOTOMAE OMP II | .......... | .......... | .......... | .......... | .......... | .......... | 2010 |
| B.2308 OMP II | .......... | .......... | .......... | .......... | .......... | .......... | 2010 |
| CONSENSUS | AATGGCTATT | CAAAATTCTG | GCRATTCTTG | ACTGGAGGTC | AGAAATGAAC | ATCAAGAGCC | 2100 |
| B.OVIS 1ST OMP II | .......... | .......... | ..A....... | .......... | .......... | .......... | 2085 |
| B.SUIS OMP II | .......... | .......... | ..G....... | .......... | .......... | .......... | 2070 |
| B.B5 OMP II | .......... | .......... | ..G....... | .......... | .......... | .......... | 2070 |
| B.MELIT 1ST OMP II | .......... | .......... | ..G....... | .......... | .......... | .......... | 2069 |
| B.CANIS OMP II | .......... | .......... | ..G....... | .......... | .......... | .......... | 2070 |
| B.NEOTOMAE OMP II | .......... | .......... | ..G....... | .......... | .......... | .......... | 2070 |
| B.2308 OMP II | .......... | .......... | ..G....... | .......... | .......... | .......... | 2070 |
| CONSENSUS | TTCTCCTTGG | CTCCGCYGCA | GCTCTGGTTG | CAGCTTCCGG | CGCTCARGCT | GCCGACGCAA | 2160 |
| B.OVIS 1ST OMP II | .......... | ......T... | .......... | .......... | ......A... | .......... | 2145 |
| B.SUIS OMP II | .......... | ......T... | .......... | .......... | ......G... | .......... | 2130 |
| B.B5 OMP II | .......... | ......T... | .......... | .......... | ......G... | .......... | 2130 |
| B.MELIT 1ST OMP II | .......... | ......C... | .......... | .......... | ......G... | .......... | 2129 |
| B.CANIS OMP II | .......... | ......T... | .......... | .......... | ......G... | .......... | 2130 |
| B.NEOTOMAE OMP II | .......... | ......T... | .......... | .......... | ......G... | .......... | 2130 |
| B.2308 OMP II | .......... | ......T... | .......... | .......... | ......G... | .......... | 2130 |

FIG. 2 I

| | | | | | | | |
|---|---|---|---|---|---|---|---|
| CONSENSUS | TCGTCGCGCC | RGAGCCCGAA | GCCGTTGAAT | ATGTCCGCGT | TTGCGACGCT | TAYGGCGCTG | 2220 |
| B.OVIS 1ST OMP II | .......... | A......... | .......... | .......... | .......... | ..T....... | 2205 |
| B.SUIS OMP II | .......... | A......... | .......... | .......... | .......... | ..C....... | 2190 |
| B.B5 OMP II | .......... | A......... | .......... | .......... | .......... | ..C....... | 2190 |
| B.MELIT 1ST OMP II | .......... | A......... | .......... | .......... | .......... | ..C....... | 2189 |
| B.CANIS OMP II | .......... | A......... | .......... | .......... | .......... | ..C....... | 2190 |
| B.NEOTOMAE OMP II | .......... | G......... | .......... | .......... | .......... | ..C....... | 2190 |
| B.2308 OMP II | .......... | A......... | .......... | .......... | .......... | ..C....... | 2190 |
| CONSENSUS | GCTACTTCTA | CATTCCGGGC | ACCGAAACCT | GCCTGCGCRT | CMRYGGYTAC | GTCCGTTACG | 2280 |
| B.OVIS 1ST OMP II | .......... | .......... | .......... | ........A. | .AGC..C... | .......... | 2265 |
| B.SUIS OMP II | .......... | .......... | .......... | ........G. | .CAT..T... | .......... | 2250 |
| B.B5 OMP II | .......... | .......... | .......... | ........G. | .CAT..T... | .......... | 2250 |
| B.MELIT 1ST OMP II | .......... | .......... | .......... | ........G. | .CAT..T... | .......... | 2249 |
| B.CANIS OMP II | .......... | .......... | .......... | ........G. | .CAT..T... | .......... | 2250 |
| B.NEOTOMAE OMP II | .......... | .......... | .......... | ........A. | .AGC..C... | .......... | 2250 |
| B.2308 OMP II | .......... | .......... | .......... | ........G. | .CAT..T... | .......... | 2250 |
| CONSENSUS | ACGTAAAGGG | CGGCGAYGAC | GTTTAYWCCG | GYWCSGAYCG | YAAWGGCTGG | GACAAGGGYG | 2340 |
| B.OVIS 1ST OMP II | .......... | ......C... | .....TA... | .CT.G..T.. | T..A...... | ........T. | 2325 |
| B.SUIS OMP II | .......... | ......C... | .....TA... | .CT.G..T.. | T..A...... | ........C. | 2310 |
| B.B5 OMP II | .......... | ......T... | .....CT... | .TA.C..C.. | C..T...... | ........C. | 2310 |
| B.MELIT 1ST OMP II | .......... | ......T... | .....CT... | .TA.C..C.. | C..T...... | ........C. | 2309 |
| B.CANIS OMP II | .......... | ......C... | .....TA... | .CT.G..T.. | T..A...... | ........C. | 2310 |
| B.NEOTOMAE OMP II | .......... | ......C... | .....TA... | .CT.G..T.. | T..A...... | ........C. | 2310 |
| B.2308 OMP II | .......... | ......T... | .....CT... | .TA.C..C.. | C..T...... | ........C. | 2310 |
| CONSENSUS | CTCGTTTYGC | ACTCATGTTC | AACACGAATT | CGGAAACCGA | ACTCGGCACA | CTCGGCACCT | 2400 |
| B.OVIS 1ST OMP II | .......T.. | .......... | .......... | .......... | .......... | .......... | 2385 |
| B.SUIS OMP II | .......C.. | .......... | .......... | .......... | .......... | .......... | 2370 |
| B.B5 OMP II | .......C.. | .......... | .......... | .......... | .......... | .......... | 2370 |
| B.MELIT 1ST OMP II | .......C.. | .......... | .......... | .......... | .......... | .......... | 2369 |
| B.CANIS OMP II | .......C.. | .......... | .......... | .......... | .......... | .......... | 2370 |
| B.NEOTOMAE OMP II | .......C.. | .......... | .......... | .......... | .......... | .......... | 2370 |
| B.2308 OMP II | .......C.. | .......... | .......... | .......... | .......... | .......... | 2370 |

FIG. 2 J

```
CONSENSUS             ATACTCAGCT GCGCTTCAAC TACACCAGCA ACAATTCACG TCATGATGGC CAATACGGCG  2460

B.OVIS 1ST OMP II     .......... .......... .......... .......... .......... ..........  2445
B.SUIS OMP II         .......... .......... .......... .......... .......... ..........  2430
B.B5 OMP II           .......... .......... .......... .......... .......... ..........  2430
B.MELIT 1ST OMP II    .......... .......... .......... .......... .......... ..........  2429
B.CANIS OMP II        .......... .......... .......... .......... .......... ..........  2430
B.NEOTOMAE OMP II     .......... .......... .......... .......... .......... ..........  2430
B.2308 OMP II         .......... .......... .......... .......... .......... ..........  2430

CONSENSUS             ATTTCAGCGA TGATCGTGAT GTCGCTGATG GCRGCGTAAN NNNNNNNNNN NNNNNNNNNN  2520

B.OVIS 1ST OMP II     .......... .......... .......... ..R......G CACCGGCACC GATCTGCAGT  2505
B.SUIS OMP II         .......... .......... .......... ..G......G CACCGGCACC GATCTGCAGT  2490
B.B5 OMP II           .......... .......... .......... ..G......G CACCGGCACC GATCTGCAGT  2490
B.MELIT 1ST OMP II    .......... .......... .......... ..G......G CACCGGCACC GATCTGCAGT  2489
B.CANIS OMP II        .......... .......... .......... ..G......G CACCGGCACC GATCTGCAGT  2490
B.NEOTOMAE OMP II     .......... .......... .......... ..G......G CACCGGCACC GATCTGCAGT  2490
B.2308 OMP II         .......... .......... .......... ..G....... .......... ..........  2490

CONSENSUS             NNNNNNNNNN NNNNNNNNNN NNNNNNNNNN NNNNNNNNNN NNNNNNNNNN NNNNNNNNNN  2580

B.OVIS 1ST OMP II     TTGCATATAT CACGCTTGGT GGTTTCAAGG TTGGTATCGA CGAATCCGAA TTCCATACCT  2565
B.SUIS OMP II         TTGCATATAT CACGCTTGGT GGTTTCAAGG TTGGTATCGA CGAATCCGAA TTCCATACCT  2550
B.B5 OMP II           TTGCATATAT CACGCTTGGT GGTTTCAAGG TTGGTATCGA CGAATCCGAA TTCCATACCT  2550
B.MELIT 1ST OMP II    TTGCATATAT CACGCTTGGT GGTTTCAAGG TTGGTATCGA CGAATCCGAA TTCCATACCT  2550
B.CANIS OMP II        TTGCATATAT CACGCTTGGT GGTTTCAAGG TTGGTATCGA CGAATCCGAA TTCCATACCT  2549
B.NEOTOMAE OMP II     TTGCATATAT CACGCTTGGT GGTTTCAAGG TTGGTATCGA CGAATCCGAA TTCCATACCT  2550
B.2308 OMP II         .......... .......... .......... .......... .......... ..........  2550

CONSENSUS             NNNNNNNNNN NNNNNNNNNN NNNNNNNNNN NNNNNNNNNN NNNNNNNNNN NNNNNNNGCA  2640

B.OVIS 1ST OMP II     TCACCGGTTA CCTCGGTGAT ATCATCAACG ATGACGTGAT CTCGGCTGGC TCCTAACC...  2625
B.SUIS OMP II         TCACCGGTTA CCTCGGTGAT GTCATCAACG ATGATGTCGT CGCTGCTGGC TCCTAACC...  2610
B.B5 OMP II           TCACCGGTTA CCTCGGTGAT GTCATCAACG ATGATGTCGT CGCTGCTGGC TCCTAACC...  2610
B.MELIT 1ST OMP II    TCACCGGTTA CCTCGGTGAT GTCATCAACG ATGATGTCGT CGCTGCTGGC TCCTAACC...  2610
B.CANIS OMP II        TCACCGGTTA CCTCGGTGAT GTCATCAACG ATGATGTCGT CGCTGCTGGC TCCTAACC...  2609
B.NEOTOMAE OMP II     TCACCGGTTA CCTCGGTGAT GTCATCAACG ATGATGTCGT CGCTGCTGGC TCCTAACC...  2610
B.2308 OMP II         .......... .......... .......... .......... .......... ..........  2610
```

FIG. 2 K

| | | | | | | | |
|---|---|---|---|---|---|---|---|
| CONSENSUS | CCGGCAAGAT | CGCCTACACC | TTCACCGGCG | GAAACGGCTT | CYCGGCTGTG | ATCGCTCTCG | 2700 |
| B.OVIS 1ST OMP II | .......... | .......... | .......... | .......... | .T........ | .......... | 2685 |
| B.SUIS OMP II | .......... | .......... | .......... | .......... | .T........ | .......... | 2670 |
| B.B5 OMP II | .......... | .......... | .......... | .......... | .T........ | .......... | 2670 |
| B.MELIT 1ST OMP II | .......... | .......... | .......... | .......... | .T........ | .......... | 2669 |
| B.CANIS OMP II | .......... | .......... | .......... | .......... | .T........ | .......... | 2670 |
| B.NEOTOMAE OMP II | .......... | .......... | .......... | .......... | .C........ | .......... | 2670 |
| B.2308 OMP II | .......... | .......... | .......... | .......... | .T........ | .......... | 2670 |
| CONSENSUS | AACAGGGTGG | CGAAGACGTT | GACAACGATT | ACACGATCGA | CGGTTACATG | CCGCACGTTG | 2760 |
| B.OVIS 1ST OMP II | .......... | .......... | .......... | .......... | .......... | .......... | 2745 |
| B.SUIS OMP II | .......... | .......... | .......... | .......... | .......... | .......... | 2730 |
| B.B5 OMP II | .......... | .......... | .......... | .......... | .......... | .......... | 2730 |
| B.MELIT 1ST OMP II | .......... | .......... | .......... | .......... | .......... | .......... | 2729 |
| B.CANIS OMP II | .......... | .......... | .......... | .......... | .......... | .......... | 2730 |
| B.NEOTOMAE OMP II | .......... | .......... | .......... | .......... | .......... | .......... | 2730 |
| B.2308 OMP II | .......... | .......... | .......... | .......... | .......... | .......... | 2730 |
| CONSENSUS | TTGGCGGCCT | GAAATATGCT | GGCGGCYGGG | GTTCGATCGC | TGGTGYTGTT | GCCTAYGACY | 2820 |
| B.OVIS 1ST OMP II | .......... | .......... | ......T... | .......... | .....T.... | .....T...T | 2805 |
| B.SUIS OMP II | .......... | .......... | ......T... | .......... | .....C.... | .....T...C | 2790 |
| B.B5 OMP II | .......... | .......... | ......T... | .......... | .....T.... | .....T...T | 2790 |
| B.MELIT 1ST OMP II | .......... | .......... | ......C... | .......... | .....T.... | .....T...T | 2789 |
| B.CANIS OMP II | .......... | .......... | ......T... | .......... | .....T.... | .....C...T | 2790 |
| B.NEOTOMAE OMP II | .......... | .......... | ......T... | .......... | .....T.... | .....T...T | 2790 |
| B.2308 OMP II | .......... | .......... | ......T... | .......... | .....T.... | .....T...T | 2790 |
| CONSENSUS | CGGTCATCGA | AGAATGGGCT | ACAAAGGTTC | GTGGCGACGT | CAACATCACC | GACCGGTTCT | 2880 |
| B.OVIS 1ST OMP II | .......... | .......... | .......... | .......... | .......... | .......... | 2865 |
| B.SUIS OMP II | .......... | .......... | .......... | .......... | .......... | .......... | 2850 |
| B.B5 OMP II | .......... | .......... | .......... | .......... | .......... | .......... | 2850 |
| B.MELIT 1ST OMP II | .......... | .......... | .......... | .......... | .......... | .......... | 2849 |
| B.CANIS OMP II | .......... | .......... | .......... | .......... | .......... | .......... | 2850 |
| B.NEOTOMAE OMP II | .......... | .......... | .......... | .......... | .......... | .......... | 2850 |
| B.2308 OMP II | .......... | .......... | .......... | .......... | .......... | .......... | 2850 |

FIG. 2 L

```
CONSENSUS             CGGTATGGCT GCAGGGCGCA TATTCGTCCG CAGCGACGCC GAACCAGAAC TACGGTCAGT  2940

B.OVIS 1ST OMP II     .......... .......... .......... .......... .......... ..........  2925
B.SUIS OMP II         .......... .......... .......... .......... .......... ..........  2910
B.B5 OMP II           .......... .......... .......... .......... .......... ..........  2910
B.MELIT 1ST OMP II    .......... .......... .......... .......... .......... ..........  2909
B.CANIS OMP II        .......... .......... .......... .......... .......... ..........  2910
B.NEOTOMAE OMP II     .......... .......... .......... .......... .......... ..........  2910
B.2308 OMP II         .......... .......... .......... .......... .......... ..........  2910

CONSENSUS             GGGGCGGCGA TTGGGCTGTC TGGGGTGGTG CAAAGTTCAT TGCCMCCGAA AAGGYAACCT  3000

B.OVIS 1ST OMP II     .......... .......... .......... .......... ....A..... ....C.....  2985
B.SUIS OMP II         .......... .......... .......... .......... ....A..... ....T.....  2970
B.B5 OMP II           .......... .......... .......... .......... ....C..... ....C.....  2970
B.MELIT 1ST OMP II    .......... .......... .......... .......... ....C..... ....C.....  2969
B.CANIS OMP II        .......... .......... .......... .......... ....A..... ....C.....  2970
B.NEOTOMAE OMP II     .......... .......... .......... .......... ....A..... ....C.....  2970
B.2308 OMP II         .......... .......... .......... .......... ....C..... ....C.....  2970

CONSENSUS             TCAATCYGCA GGCTGCGCAT GACGACTGGG GCAAGACSGC AGTTACSGCY AACGTYGCTT  3060

B.OVIS 1ST OMP II     ......C... .......... .......... .......C.. ......C..C .....C....  3045
B.SUIS OMP II         ......T... .......... .......... .......C.. ......C..C .....C....  3030
B.B5 OMP II           ......T... .......... .......... .......C.. ......C..C .....C....  3030
B.MELIT 1ST OMP II    ......T... .......... .......... .......C.. ......C..C .....C....  3029
B.CANIS OMP II        ......T... .......... .......... .......C.. ......C..C .....C....  3030
B.NEOTOMAE OMP II     ......T... .......... .......... .......G.. ......G..T .....T....  3030
B.2308 OMP II         ......T... .......... .......... .......C.. ......C..C .....C....  3030

CONSENSUS             AYSARCTSGT TCCYGGMTTC ACCRTTACGC CGGAAGTTTC CTACACCAAA TTTGGTGGCG  3120

B.OVIS 1ST OMP II     .TC.G..C.. ...C..A... ...A...... .......... .......... ..........  3105
B.SUIS OMP II         .TC.G..C.. ...C..A... ...A...... .......... .......... ..........  3090
B.B5 OMP II           .TC.G..C.. ...C..A... ...A...... .......... .......... ..........  3090
B.MELIT 1ST OMP II    .TC.G..C.. ...C..A... ...A...... .......... .......... ..........  3089
B.CANIS OMP II        .TC.G..C.. ...C..A... ...A...... .......... .......... ..........  3090
B.NEOTOMAE OMP II     .CG.A..G.. ...T..C... ...G...... .......... .......... ..........  3090
B.2308 OMP II         .TC.G..C.. ...C..A... ...A...... .......... .......... ..........  3090
```

FIG. 2 M

```
CONSENSUS             AGTRGAAAGA CACCGTTGCT GAAGACAATG CCTGGGGCGG TATCGTTCGC TTCCAGCGCT  3180

B.OVIS 1ST OMP II     ...A...... .......... .......... .......... .......... ..........  3165
B.SUIS OMP II         ...G...... .......... .......... .......... .......... ..........  3150
B.B5 OMP II           ...G...... .......... .......... .......... .......... ..........  3150
B.MELIT 1ST OMP II    ...A...... .......... .......... .......... .......... ..........  3149
B.CANIS OMP II        ...G...... .......... .......... .......... .......... ..........  3150
B.NEOTOMAE OMP II     ...G...... .......... .......... .......... .......... ..........  3150
B.2308 OMP II         ...G...... .......... .......... .......... .......... ..........  3150

CONSENSUS             CGTTCTAATC AGATCGACGT TAAGCATAGG GCGCCAACGG TTTCCCGTTG GCGCCGGTTC  3240

B.OVIS 1ST OMP II     .......... .......... .......... .......... .......... ..........  3225
B.SUIS OMP II         .......... .......... .......... .......... .......... ..........  3210
B.B5 OMP II           .......... .......... .......... .......... .......... ..........  3210
B.MELIT 1ST OMP II    .......... .......... .......... .......... .......... ..........  3209
B.CANIS OMP II        .......... .......... .......... .......... .......... ..........  3210
B.NEOTOMAE OMP II     .......... .......... .......... .......... .......... ..........  3210
B.2308 OMP II         .......... .......... .......... .......... .......... ..........  3210

CONSENSUS             ATTTGAAACA GCGTTCACGA AAGCGTGAGA ATCGATTCTT CCGGAATGGG GATTCCAGGC  3300

B.OVIS 1ST OMP II     .......... .......... .......... .......... .......... ..........  3285
B.SUIS OMP II         .......... .......... .......... .......... .......... ..........  3270
B.B5 OMP II           .......... .......... .......... .......... .......... ..........  3270
B.MELIT 1ST OMP II    .......... .......... .......... .......... .......... ..........  3269
B.CANIS OMP II        .......... .......... .......... .......... .......... ..........  3270
B.NEOTOMAE OMP II     .......... .......... .......... .......... .......... ..........  3270
B.2308 OMP II         .......... .......... .......... .......... .......... ..........  3270

CONSENSUS             GGATCGACAA TTGAGGGAAT TGCGGGGACG ACAAAAAGCT GGGGGCAACC GGGGGGTCTT  3360

B.OVIS 1ST OMP II     .......... .......... .......... .......... .......... ..........  3345
B.SUIS OMP II         .......... .......... .......... .......... .......... ..........  3330
B.B5 OMP II           .......... .......... .......... .......... .......... ..........  3330
B.MELIT 1ST OMP II    .......... .......... .......... .......... .......... ..........  3329
B.CANIS OMP II        .......... .......... .......... .......... .......... ..........  3330
B.NEOTOMAE OMP II     .......... .......... .......... .......... .......... ..........  3330
B.2308 OMP II         .......... .......... .......... .......... .......... ..........  3330
```

FIG. 2 N

| | | | |
|---|---|---|---|
| CONSENSUS | GTAAAGGATT | GAGCCA | 3376 |
| B.OVIS 1ST OMP II | .......... | ...... | 3361 |
| B.SUIS OMP II | .......... | ...... | 3346 |
| B.B5 OMP II | .......... | ...... | 3346 |
| B.MELIT 1ST OMP II | .......... | ...... | 3345 |
| B.CANIS OMP II | .......... | ...... | 3346 |
| B.NEOTOMAE OMP II | .......... | ...... | 3346 |
| B.2308 OMP II | .......... | ...... | 3346 |

FIG.10
PROBE 1(C)
—B. MELITENSIS
—B. BIOVAR 5
—B. CANIS
—B. SUIS
—B. OVIS
—B. NEOTOMAE
—B. 2308
—pAGF201
37°C— 
65°C— 

PROBES AND METHOD FOR IDENTIFYING SPECIES AND BIOVARS OF BRUCELLA

This is a continuation-in-part of U.S. Ser. No. 07/527,017 filed May 22, 1990.

FIELD OF THE INVENTION

This invention relates to a method for the diagnostic identification of the pathogenic bacterium Brucella, and more specifically to novel oligonucleotide probes and methods to identify a species and biovar of Brucella.

BACKGROUND OF THE INVENTION

Brucella is a genus of pathogenic bacteria which cause acute or chronic illness in many animal species, including humans and cattle. Six species of and multiple biovars have been characterized by phenotypic methods, although such methods are not always reliable. The six species and multiple biovars of Brucella may also be characterized by their natural host and a strain's geographical origin (See Table 1), however, a species may infect an animal other than fits natural host, and a single strain may now be found fin multiple geographic locations.

Early detection and characterization of the species or biovar of the infecting Brucella organism would be of great value in medical and veterinary practice. Rapid and reliable detection of Brucella infection is important to permit removal of infected animals from a healthy herd and prevent the spread of the disease. Characterization of the species or biovar of Brucella would provide epidemiological data to determine the source of the infection.

TABLE 1

| SPECIES | BIOVAR | STRAIN | HOST | ORIGIN |
|---|---|---|---|---|
| *B. abortus* | 1 | 19 | | U.S. |
| | 1 | 2308 | cattle | U.S. |
| | 1 | RB51 | d.2308[a] | U.S. |
| | 1 | 45/20 | d.45/0 | England |
| | 2 | ATCC 23449 | cattle/ bison | England |
| | 3 | ATCC 23450 | cattle/ bison | Uganda |
| | 4 | ATCC 23451 | cattle/ bison | England |
| | 5 | ATCC 23452 | cattle/ bison | England |
| | 6 | ATCC 23453 | cattle/ bison | Africa |
| | 7 | ATCC 23454 | cattle/ bison | |
| | 9 | ATCC 23455 | cattle/ bison | England |
| *B. melitensis* | 1 | ATCC 23456 | goat | U.S. |
| *B. suis* | 1 | ATCC 23444 | pig | U.S. |
| *B. neotomae* | | ATCC 23459 | desert wood rat | U.S. |
| *B. canis* | | ATCC 23365 | dog | U.S. |
| *B. ovis* | | ATCC 25840 | sheep | Africa |

ATCC - American Type Culture Collection, Bethesda, Maryland.
d. - derivative

Heretofore, standard serological tests used to detect Brucella have required several weeks time to complete and have not always been able to distinguish between species of Brucella. The methods currently available to identify species of infecting Brucella require the isolation of bacteria on selective media followed by quantitative analysis of phenotypic properties of the organism. Phenotypic characterization may be based on such features as lipopolysaccharide antigens, phage typing, dye sensitivities, $CO_2$ requirements, $H_2S$ production, and metabolic properties. Such methods are time consuming (requiring 1–4 weeks) and are unreliable. (see Alton, 1988, *Techniques for the Brucellosis Laboratory*; Moriera-Jacob, 1963, *Nature* 197: 406; Shibata, 1962, *Nat. Inst. Anim. Health Q.* 2: 10–14) Time delays in obtaining test results and uncertainty due to unreliable test results can result in great economic losses. Suspect animals may require quarantine or may contaminate healthy animals in the herd during the waiting period.

Identification of Brucella species using DNA probes has not previously been possible, due to the high degree of inter-species DNA homology (approximately 90%).

There remains a great need for a rapid and accurate method for detecting the presence of pathogenic Brucella organisms in a suspect animal. It is also greatly desirable that such a detection method have the ability to distinguish between and identify the species and/or biovars of Brucella.

SUMMARY OF THE INVENTION

The method of the present invention solves the problems of the prior art methods by providing a rapid, sensitive, and accurate diagnostic method for the detection of Brucella and, more specifically a diagnostic method which is able to distinguish between species and biovars of Brucella.

It has now been found that the omp2 gene locus is conserved in all species of Brucella. Rapid detection of Brucella is achieved by identification of the conserved omp2 gene locus.

It has also been found that genetic variation at the omp2 gene locus of Brucella correlates with established species designations, and that this genetic variation may be used as a stable diagnostic marker for particular species of Brucella. Differentiation between species and biovars is based upon analysis of restriction fragment length polymorphism in the omp2 gene locus of Brucella.

A preferred embodiment of the method of the present invention includes amplification of the omp2 gene locus. The amplified omp2 gene locus may then be analyzed directly by electrophoretic separation, dot blot or Southern Blot analysis to enable diagnosis of Brucella infection. Alternatively, restriction digestion of the amplified omp2 gene releases fragments which may be analyzed, for example by gel electrophoresis, and the restriction fragment pattern used to detect the presence of Brucella and to identify the species or biovar of Brucella.

In the preferred embodiment, novel DNA probes which hybridize to the omp2 gene locus are used to enable diagnosis of Brucella infection, and additional DNA probes having specific hybridization characteristics are used to identify the species or biovar of Brucella.

DESCRIPTION OF THE DRAWINGS

FIG. 1 is a partial restriction map of the omp2 locus of the different Brucella species and biovar groups.

FIGS. 2A–O are an aligned sequence listing of the omp2 gene locus of different species and biovars of Brucella, with underlined sequences depicting oligonucleotides useful as diagnostic probes.

FIG. 3 is a partial restriction map of the omp2 locus of *Brucella abortus*.

FIG. 8 is a Southern Blot of amplified Brucella omp2 DNA hybridized with the diagnostic probe 1a.

FIG. 10 is a Southern Blot of amplified Brucella omp2 DNA hybridized with the diagnostic probe 1c.

FIG. 11 is a Southern Blot of amplified Brucella omp2 DNA hybridized with the diagnostic probe 2a.

DETAILED DESCRIPTION OF THE INVENTION

According to the method of the present invention, animal fluids or tissues may be tested for the presence of Brucella, and the species and biovar of Brucella infecting the animal may be rapidly and accurately detected. Animal fluids and tissues including blood, urine, milk, semen, vaginal secretions, rectal secretions or other available tissues may be collected and used as the test sample, despite the presence of complex, non-Brucella DNA. The live bacteria in the sample are killed, for example by heating to 68° C. for approximately 1 to 2 hours. The cells of the sample are then lysed to release DNA, for example, by heating to approximately 95° C. for approximately ten minutes or by repeated freezing and thawing of the cells. It may be desirable to immobilize the released DNA on a solid support in order to concentrate the DNA. For example, the DNA released by the lysed cells may be collected and concentrated in an agarose gel, or on a nitrocellulose filter.

A desired gene sequence in the DNA released from the lysed cells is then amplified, preferably through 30 to 50 cycles, by means of standard liquid polymerase chain reaction (PCR) using commercially available cyclers or manually in changing water baths. The PCR method is known in the art, and is described, for example, in Saiki et al, *Science* 239: 487–491, 1985, which is hereby incorporated by reference. In general, the PCR amplification method includes the hybridization of a pair of oligonucleotide primers to a segment of DNA. The oligonucleotide primers are designed to anneal to the DNA sequences flanking the target gene sequence that is to be amplified, with one oligonucleotide upstream and one downstream of the target sequence, on opposing DNA strands. During each amplification cycle, DNA strands are separated, for example by heating, priming oligonucleotides are annealed, for example by cooling the heated DNA in the presence of the oligonucleotides, and the primers are extended using DNA polymerases and adding nucleotides to the end of each primer to make copies of the target DNA sequence. This process is repeated through approximately 30–50 amplification cycles, geometrically increasing the number of copies of the target gene sequence.

Figure 1:
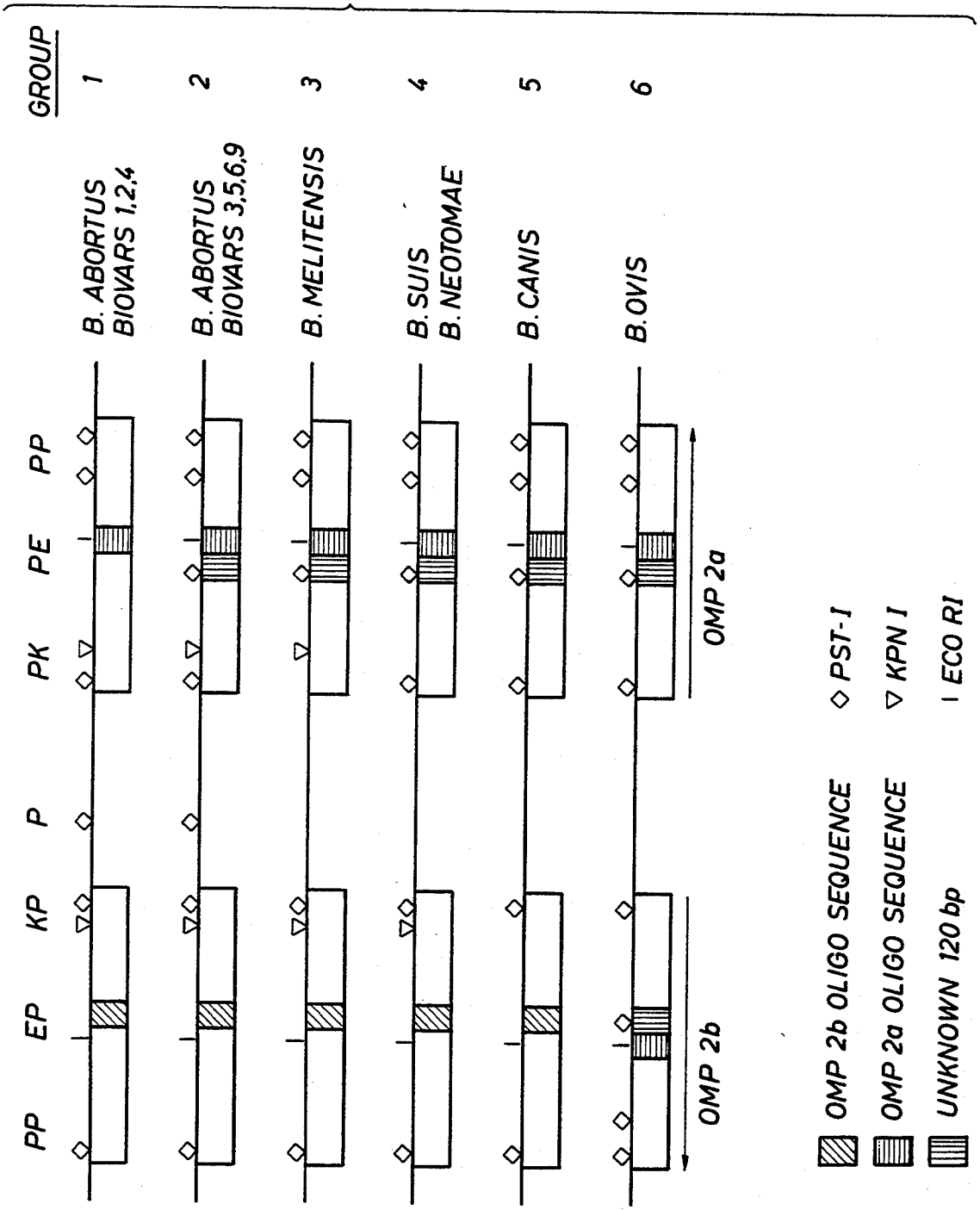

Specific oligonucleotides are used to prime the amplification at the omp2 gene locus. As shown in FIG. 1, the omp2 gene locus includes the omp2a and omp2b genes as well as flanking and intervening gene sequences. The DNA sequences of the omp2 gene locus of various Brucella species and biovars is shown in FIGS. 2A–O and listed as Sequence Id. Nos. 2–8. A consensus sequence (Seq. Id. No. 1) is also shown in FIGS. 2A–O.

Figure 4:
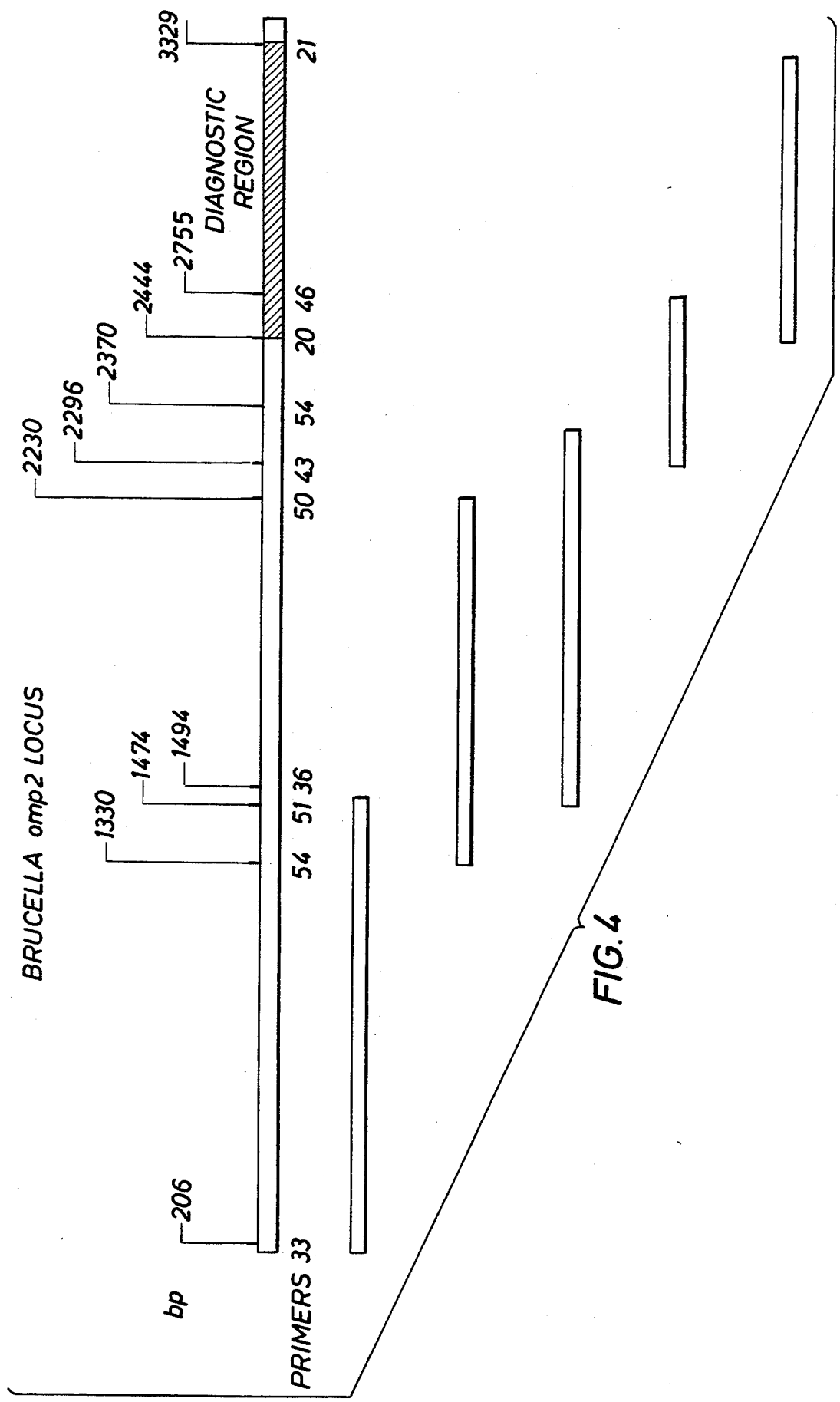
FIG. 4 is a diagram of the Brucella omp2 gene locus showing locations of amplification primers useful in the present invention.

Specific oligonucleotide pairs designed to hybridize to specific gene sequences of the omp2 gene locus permit amplification of a desired gene sequence of the omp2 gene locus. In the method of the present invention, regions of the omp2 gene locus having sufficient diversity to enable identification of Brucella species and biovars are amplified. Examples of oligonucleotides useful in the present invention include the amplification primers listed in Table 2. In FIGS. 2A–O, those oligonucleotides useful as amplification primers are overlined in the consensus sequence. Useful primers are also shown in FIG. 4. Preferred are primers which amplify the Brucella omp2 gene locus in the region approximately between base pairs 2470 and 3360 of the consensus sequence, due to o the unusually high density of species variation in this region. The primer set having Seq. Id. Nos. 19 and 20 is particularly useful to amplify this region. While it is understood that several regions of sequence diversity found in the omp2 gene locus may potentially be used to prepare diagnostic probes, the preferred DNA sequences amplified in the present invention include regions of sufficient DNA homology among Brucella species to enable PCR amplification and confirmation of identity as well as sufficient sequence diversity to permit the characterization of the specific species or biovars of Brucella.

TABLE 2

| | OLIGONUCLEOTIDE PAIRS TO AMPLIFY BRUCELLA OMP2 GENE | | |
|---|---|---|---|
| PROBE NO. | SEQUENCE ID. NO. | SEQUENCE | AMPLIFIED |
| 47 | | CGC GAA CTC CAT GAC GGT GCC GC | omp2b |
| 41 | | CCT TGG CTC CGC TGC AGC TCT GGT | |
| 32 | 11 | CAG GCG ATC TTC CGC GAC CCC | omp2b |
| 33 | 12 | GGG GAT GGG GAC AGG TTG TCC | |
| 51 | 13 | TGG GTC TGG GCA TTC TGA TTT GGC TG | intervening |
| 50 | 14 | TCG CCA GAA TTT TGA ATA GCC ATT AC | |
| 41 | 15 | CCT TGG CTC CGC TGC AGC TCT GGT | omp2a |
| 46 | 16 | CGT TGT CAA CGT CTT CGC CAC CC | |
| 34 | 17 | CCG GCG GCC AAC GGG AAA CCG | omp2a |
| 35 | 18 | CGG CTT TAC CCC TCG CGC AC | |
| 20 | 19 | TGG CTC AAT CCT TTA CAA | omp2a |
| 21 | 20 | TCG TGA TGT CGC TGA TGG | |

The amplified DNA may be analyzed directly by dot blot analysis using a labeled omp2 gene probe, by hybridization analysis using radiolabeled oligonucleotide probes, or by separating the amplified DNA, for example, using agarose gel electrophoresis and ethidium bromide staining or Southern Blot analysis to detect the amplified gene sequence. The presence of the amplified omp2 gene indicates the presence of Brucella organisms in the test sample.

In a preferred embodiment, the amplified DNA may first be digested with specific restriction enzymes to generate restriction fragments characteristic of the omp2 gene locus prior to analysis by separation and staining or hybridization to specific omp2 gene probes. Proper selection of the restriction enzyme may result in fragments displaying an electrophoretic pattern characteristic of the Brucella omp2 gene in all species of Brucella. Alternatively, the selection of restriction enzymes may result in fragments displaying restriction fragment length polymorphism (RFLP), for example, in the omp2a gene and flanking sequence of Brucella.

A preferred restriction enzyme which can be used to detect the omp2 gene in all species of Brucella is Bam HI. Restriction digestion of genomic or amplified Brucella DNA using Bam HI releases a characteristic 6.5 kb fragment containing the omp2 gene.

Preferred restriction enzymes which can be used to identify the particular species or biovar of the infecting Brucella organism include PstI and KpnI. Digestion of the amplified omp2 gene locus with PstI and/or KpnI results in restriction fragments displaying a unique electrophoretic pattern in agarose gels for *B. abortus, B. melitensis, B. canis,* and *B. ovis*. The restriction fragment patterns for *B. suis* and *B. neotomae*, while distinct from the other 4 Brucella species, are not distinguished from each other using these digestive enzymes. Biovars 1, 2, and 4 of *B. abortus* may also be identified based upon the size of the PstI restriction fragments.

The pattern of restriction fragments may be visualized in the electrophoretic gel by staining, for example, with ethidium bromide, which has a sensitivity in the range of 0.1–1.0 μg DNA. Alternatively, when the amount of DNA is limited, i.e., 0.01–0.1 μg DNA, Southern Blot or dot blot analysis with omp2 DNA probes can be used.

In a preferred embodiment, novel DNA probes are used to identify a Brucella species or biovar. These probes can be used in hybridization analysis such as dot blot or Southern blot following radioactive labeling or other method of detection, e.g., chemiluminescence or color-development. For example, oligonucleotide probes in the region amplified by the amplification primers having Seq. Id. Nos. 19 and 20 can be used to specifically diagnose a Brucella species or biovar and are shown in Table 3.

TABLE 3

| SEQ. ID. | PROBE | | |
|---|---|---|---|
| 21 | 1a | ATGTCGTCGC | TGCTGGCTCC |
| 22 | 1b | ATGTCGTCGC | TGATGGCTCC |
| 23 | 1c | ACGTGATCTC | GGCTGGCTCC |
| 24 | 2a | TGTTGTTGCC | TATGACTCGG |
| 25 | 2b | TGCTGTTGCC | TATGACCCGG |
| 26 | 3a | CCCCGAAAAG | GCAACCTTCA |
| 27 | 3b | CACCGAAAAG | GCAACCTTCA |
| 28 | 3c | CACCGAAAAG | GTAACCTTCA |
| 29 | 4a | AGACCGCAGT | TACCGCCAAC |
| 30 | 4b | AGACGGCAGT | TACGGCTAAC |
| 31 | 5a | GTCGCTTATC | AGCTCGTTCC |

TABLE 3-continued

| SEQ. ID. | PROBE | | |
|---|---|---|---|
| 32 | 5b | GTTGCTTACG | AACTGGTTCC |

In the method invention, oligonucleotide primers are used to amplify a specific region of the omp2 gene which contains sufficient diversity in DNA sequence among Brucella species and biovars to permit their identification. Oligoneucleotide probes which hybridize to sequences contained within the amplified DNA region are used to specifically identify the species and/or biovar of Brucella. It is understood that regions of species diversity in the omp2 gene locus may be used to distinguish between species and biovars of Brucella. It is preferred that the region of the omp2 gene to be used contain sufficient diversity among species and biovars of Brucella to enable identification using a minimal number of diagnostic probes.

Primers such as those having Seq. Id. Nos. 19 and 20 are used to amplify a region of the omp2 gene having sufficient diversity to enable distinction of species and biovars of Brucella. As shown in FIGS. 2A-O, DNA amplified between Seq. Id. Nos. 19 and 20 correspond to areas of the Brucella omp2 gene consensus sequence at approximately nucleotides 3358–3376 and 2444–2461, respectively. These primers amplify a region of Brucella omp2 DNA having a very high degree of diversity among species and biovars of Brucella, as shown in FIGS. 2A-O. The probes listed in Table 3 hybridize to DNA of specific species or biovars of Brucella in the region between these primers, in a pattern which permits specific identification.

TABLE 4

| | 1 | | | 2 | | 3 | | | 4 | | 5 | |
|---|---|---|---|---|---|---|---|---|---|---|---|---|
| | a | b | c | a | b | a | b | c | a | b | a | b |
| B abortus b1 | − | − | − | + | − | + | − | − | + | − | + | − |
| B abortus b5 | + | − | − | + | − | + | − | − | + | − | + | − |
| B. melitensis | + | − | − | + | − | − | + | − | + | − | + | − |
| B. suis | + | − | − | − | + | − | − | + | + | − | + | − |
| B. canis | + | − | − | − | + | − | + | − | + | − | + | − |
| B. neotomae | − | + | − | + | − | − | + | − | − | + | − | + |
| B. ovis | − | − | + | + | − | − | + | − | + | − | + | − |

A diagnostic test to distinguish among the Brucella species can be performed using a combination of these oligonucleotide probes. The basic premise is to characterize the amplification products of a PCR reaction by hybridization. Reference to Table 4 indicates use of a single probe, for example, probe 5b, may be sufficient to diagnose *B. neotomae*. Likewise, probe 3c can diagnose *B. suis*. Generally, however, the diagnosis cannot be performed with a single oligonucleotide due to the similarity in the DNA of these organisms, and thus a combination of at least two probe sets is used to distinguish Brucella species and biovars. Table 4 shows the pattern of hybridization for each of the probes listed in Table 3 with omp2 DNA of specific species and biovars of Brucella. Comparison of hybridization results of a test sample to a panel of two or more probes known to hybridize in a specific pattern with the omp2 gene of specific species and biovars of Brucella, for example, those shown in Table 4, enables identification of a specific species or biovar of Brucella in a test sample.

For example, as shown in Table 5, characterization of the amplification product of the omp2a gene via hybridization to oligonucleotide probes 1(a-c) and 3(a-c) distinguishes all Brucella species except *B. melitensis* and *B. canis*. An additional probe set, 2(a-b), distinguishes *B. melitenis* and *B. canis*. In a similar fashion, other probes identified in FIGS. 2A–O may be used in various combinations to provide a diagnostic panel of oligonucleotides to identify specific Brucella species and biovars.

TABLE 5

|  | POSITIVE HYBRIDIZATION | | |
| --- | --- | --- | --- |
|  | 1 | 2 | 3 |
| *B. abortus* b1 | — | a | a |
| *B. abortus* b5 | a | a | a |
| *B. melintensis* | a | a | b |
| *B. suis* | a | b | c |
| *B. canis* | a | b | b |
| *B. neotomae* | b | a | b |
| *B. ovis* | c | a | b |

Using the omp2 gene sequences disclosed in FIG. 2, additional regions of the omp2 gene locus may be identified for amplification or additional oligonucleotide probes may be identified for use in diagnosing Brucella infection in a manner similar to that described herein. It is also understood that the oligonucleotides disclosed herein may be modified, e.g., by shifting the sequence upstream or downstream, to attain similar amplification and probing results as described for the exemplified oligonucleotides.

The invention may be better understood by reference to the following examples.

EXAMPLES

EXAMPLE 1

Conservation of the omp2 Gene Locus in Species and Biovars of Brucella

*B. abortus* smooth strains 19 and 2308 were obtained from Dr. Billy Deyoe at the National Animal Disease Center in Ames, Iowa. *B. abortus* biovars 1–7 and 9, *B. suis*, *B. canis*, *B. neotomae*, *B. melitensis*, and *B. ovis* were obtained for the American Type Culture Collection, in Bethesda, Md. (See Table 1). Strain identification was confirmed by standard biovar analysis (see Alton, 1988). Brucella strains were cultivated on either Brucella agar or tryptic soy agar (Difco Laboratories, Detroit, Mich.). *E. Coli* cells were grown as described in Ficht, 1988, *Infect. Immunol.* 56: 2036–2046.

Brucella cells were grown on agar plates at 37° C. for approximately 48 hours. Cells were washed off the plates in 5 ml of phenol/saline (0.1% w/v and 0.85% w/v, respectively). The cells were killed by incubation for 1–2 hours at 68° C. and pelleted by centrifugation at 5000 rpm for 20 minutes. The cell pellet was resuspended in 5 ml buffer A (10 mM Tris-HCl, pH 7.6, 1M NaCl) at room temperature, pelleted again, and resuspended in a final volume of 2 ml buffer A. The cell suspension was warmed to 42° C. and diluted with an equal volume of a solution containing 1% w/v low melting point agarose (Bethesda Research Labs, -Bethesda, Md.) in sterile water. Aliquots (100–200 μl) of this mixture were poured into molds to form agarose blocks and chilled on ice. The blocks were transferred to Eppendorf tubes containing an equal volume of lysis buffer (6 mM Tris-HCl, pH 7.6, 1M NaCl, 100 mM EDTA, pH 7.5, 0.5% w/v Brij-58 (Aldrich, Milwaukee, Wis.), 0.2% w/v sodium deoxycholate, 0.5% w/v sodium N-lauroylsarcosine) made from sterile stock solutions and filter sterilized following the addition of detergents. This solution was supplemented just prior to use with 1 mg/ml lysozyme and 20 μg/ml RNase A (10 mg/ml stock in sterile dH$_2$O heated to 80° C. for 20 minutes). The cell suspension was then incubated in the lysis buffer overnight at 37° C. The following day the lysis buffer was removed and an equal volume of ESP buffer (0.5M EDTA, pH 9–9.5, 1% w/v in sodium lauryl sarcosinate, and 1.0 mg/ml proteinase K preincubated for 2 hours at 37° C.) was added. The mixture was incubated for 24–48 hours at 50° C. The gel block was then washed in 4 changes of TE buffer (50 mM Tris-HCl, 0.1 mM EDTA, pH 7.5) containing 1 mM phenyl methyl-sulfonyl fluoride (PMSF) for 4 hours at room temperature. The gel block was then washed twice for 4–16 hours with Bam HI restriction enzyme buffer (as supplied by the manufacturer, Boehringer-Mannheim, Indianapolis, Ind.) The washed block was dissolved in 0.5 ml of the restriction enzyme buffer at 65° C. for 10 minutes.

Figure 3:
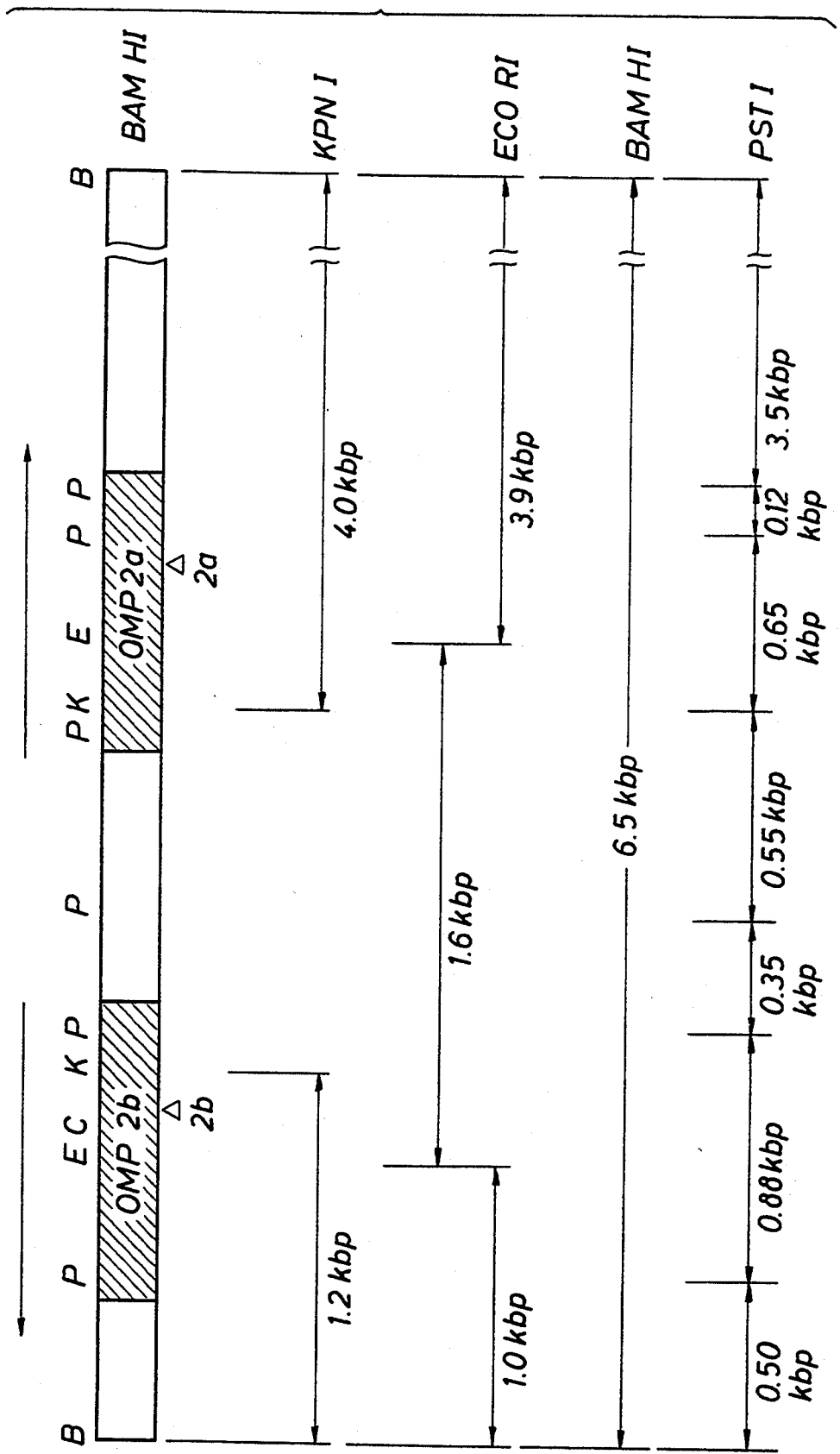
Figure 5:
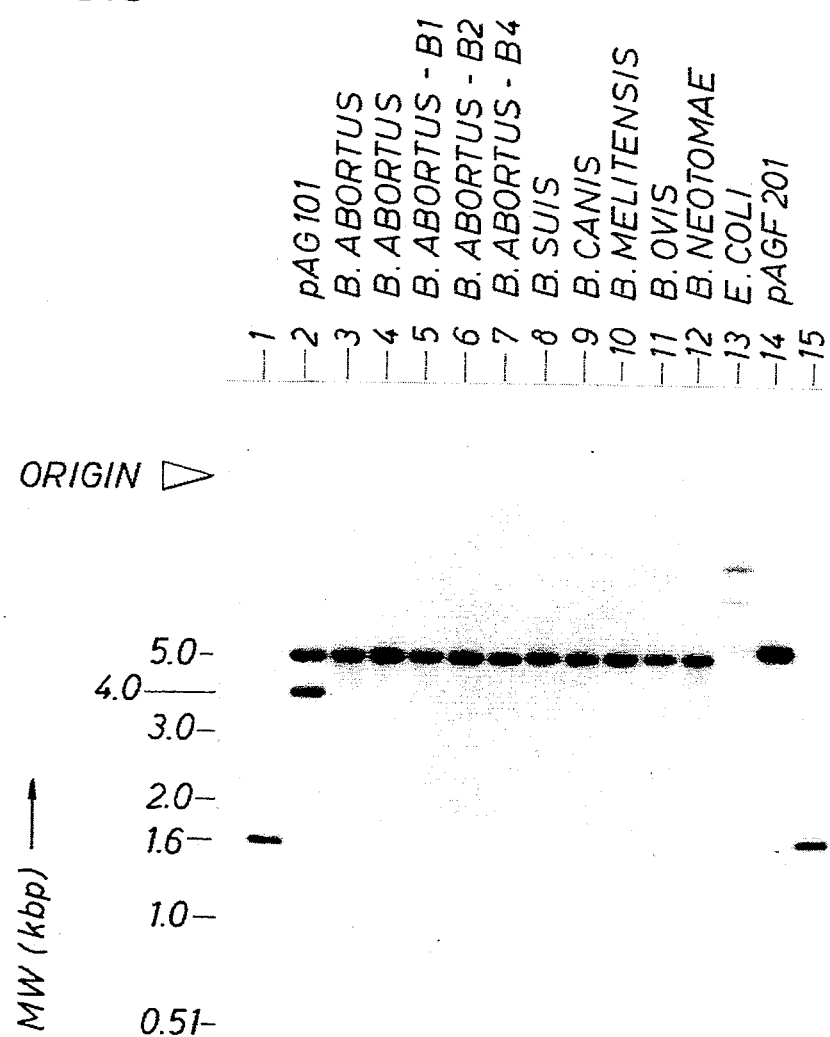
FIG. 5 is a Southern Blot of Brucella genomic DNA digested with Bam HI and hybridized with a labeled Bam HI fragment containing the omp2 gene locus of *B. abortus*.

The restriction fragments were separated in a 2% w/v agarose gel. Southern Blot analysis included the transfer of the separated restriction fragments onto nitrocellulose, and hybridization with a labeled DNA probe consisting of the Bam HI restriction fragment of the *B. abortus* omp2 gene locus, as shown in FIG. 3. The results of the Southern Blot analysis are shown in FIG. 5, and indicate that all six species of Brucella and all *B. abortus* biovars tested have conserved the omp2 locus on a 6.5 kb Bam HI fragment.

EXAMPLE 2

Heterogeneity of the omp2a Gene in Species and Biovars of Brucella

Figure 6:
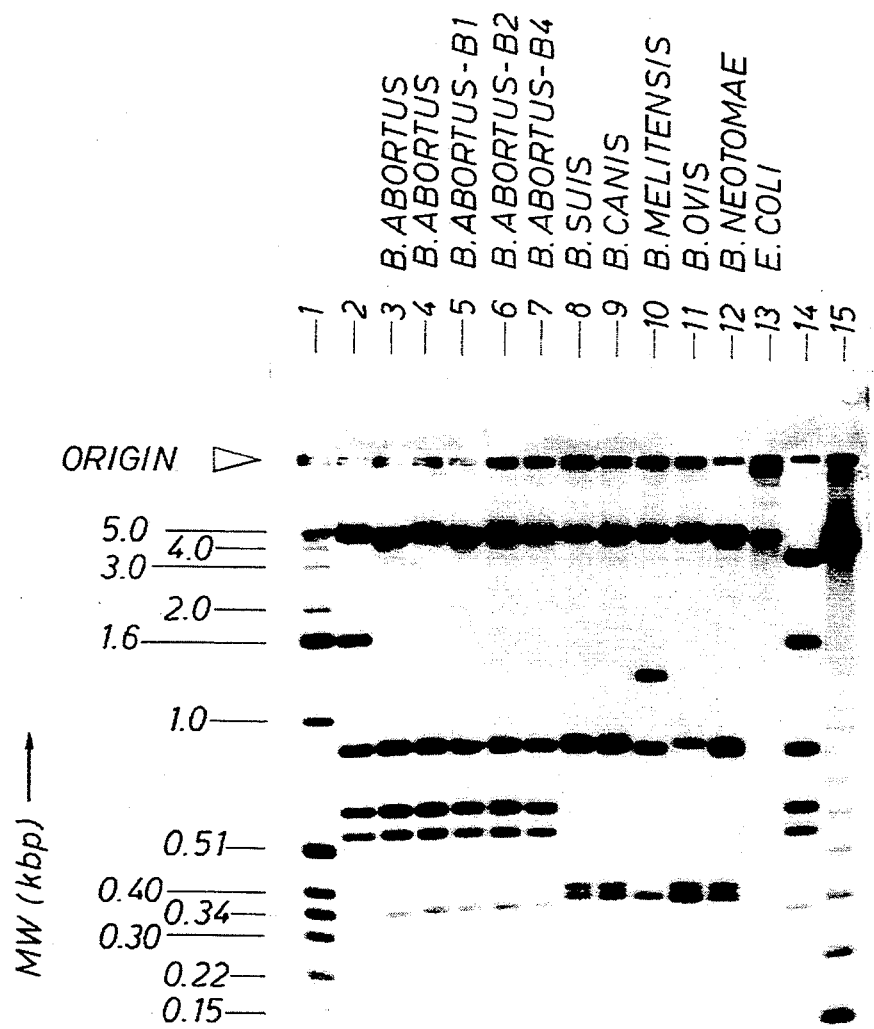
FIG. 6 is a Southern Blot of Brucella genomic DNA digested with Pst I and hybridized with a labeled Bam HI fragment containing the omp2 gene locus of *B. abortus*.
Figure 7:
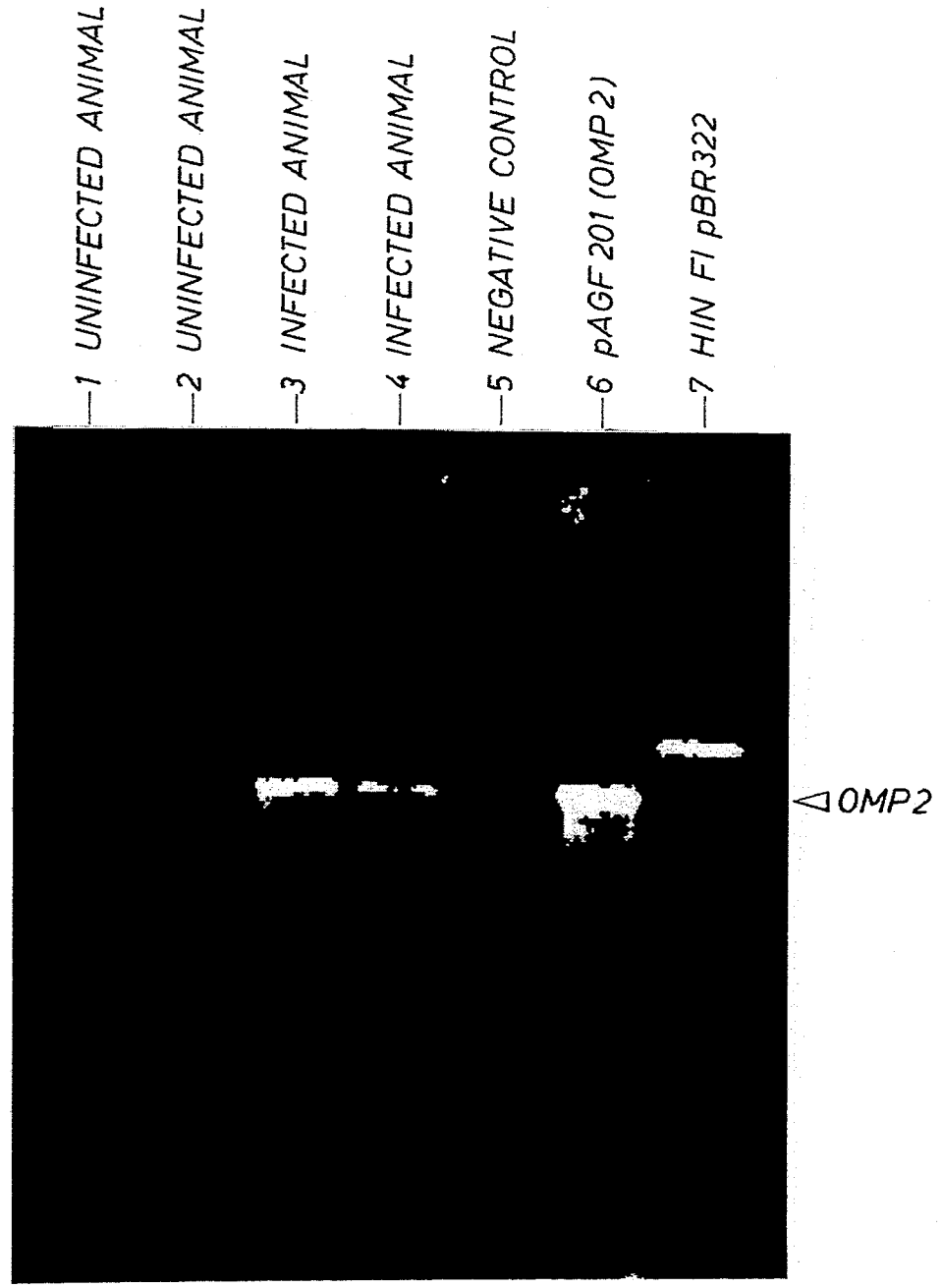
FIG. 7 is an agarose gel stained with ethidium bromide showing the presence of the amplified omp2 gene in Brucella infected versus non-infected cattle.
Figure 8:
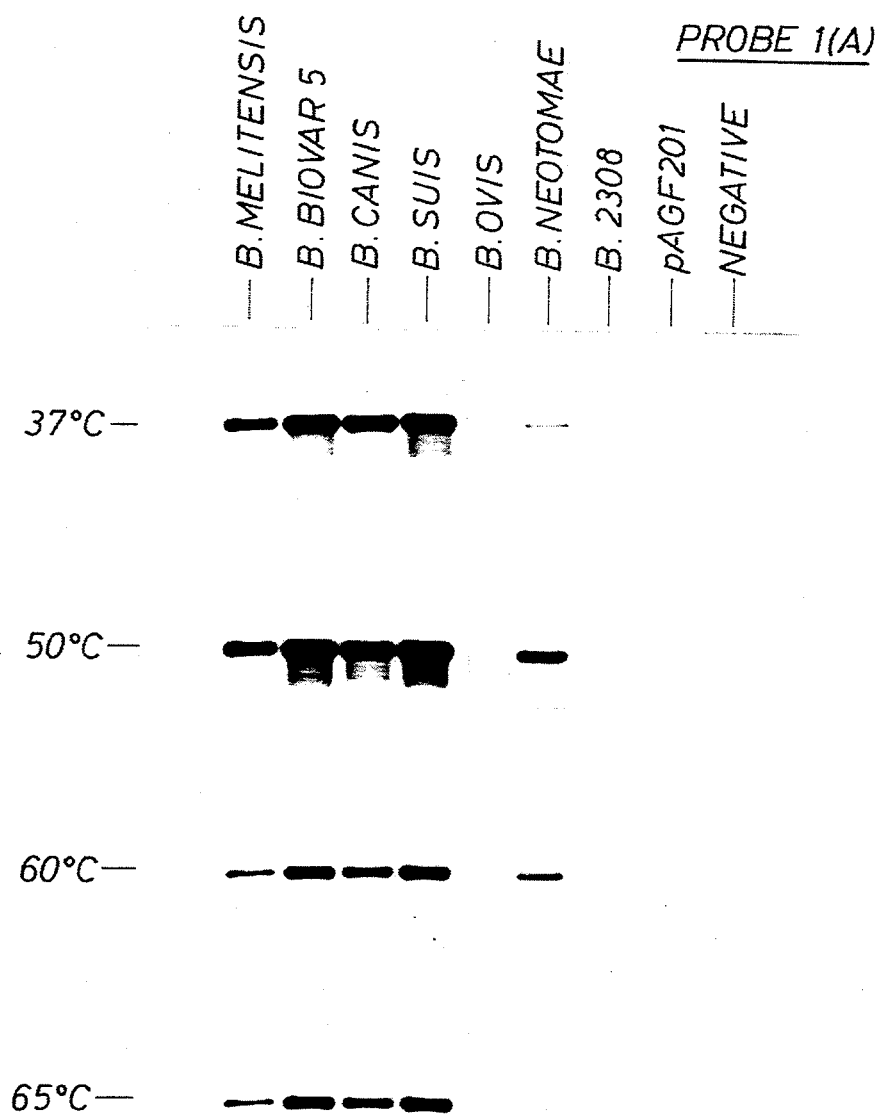
Figure 9:
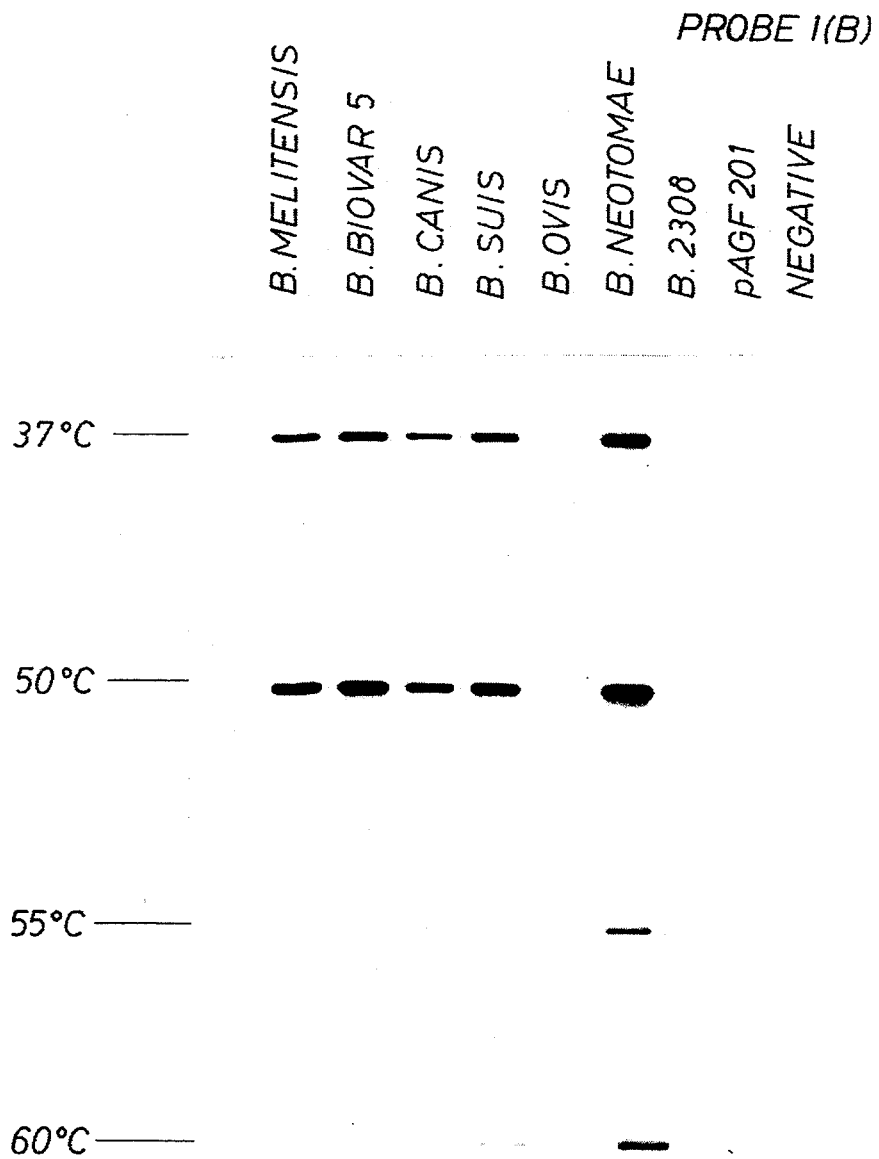
FIG. 9 is a Southern Blot of amplified Brucella omp2 DNA hybridized with the diagnostic probe 1b.
Figure 11:
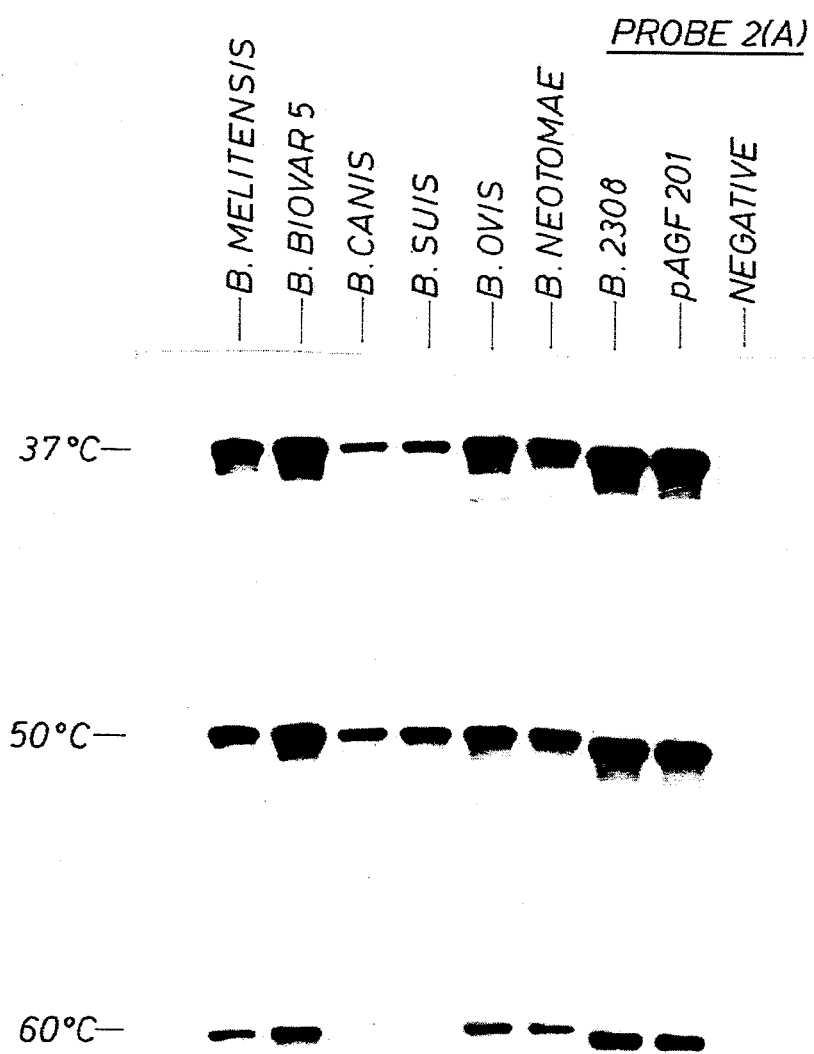
Figure 12:
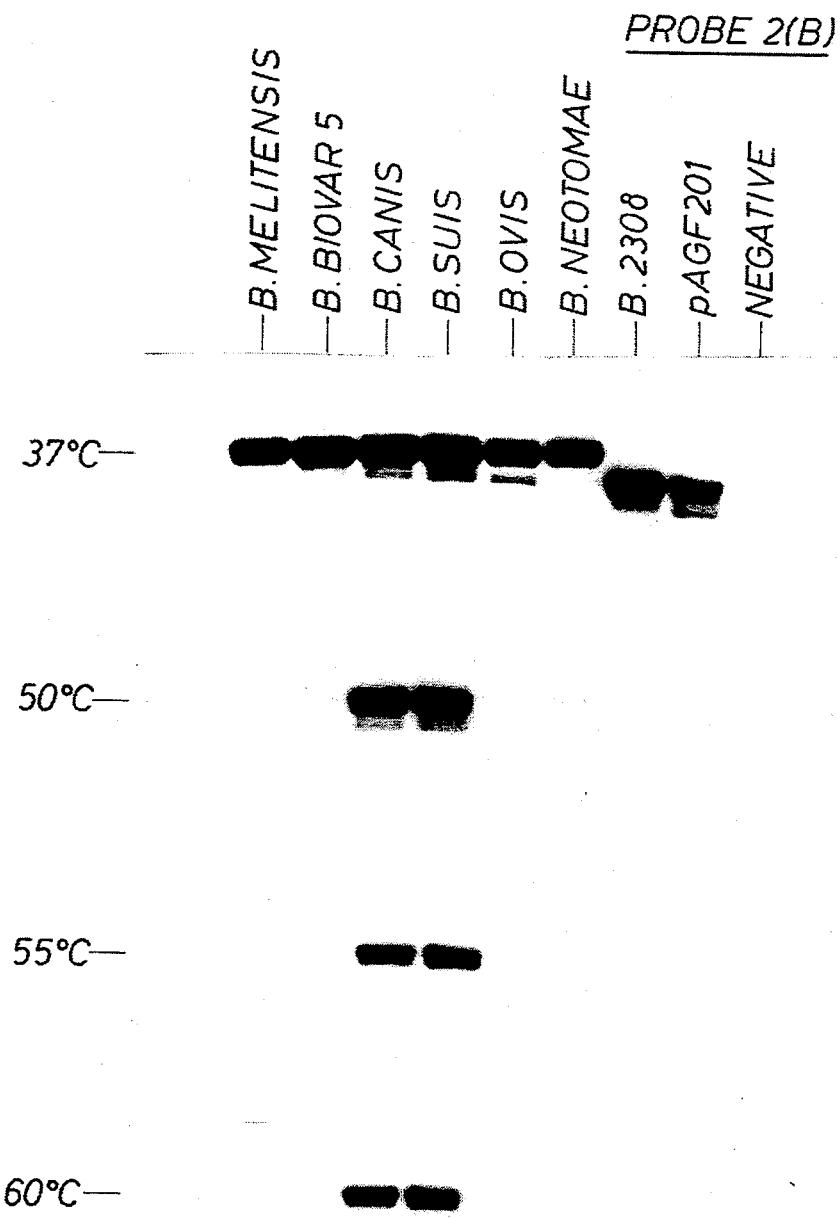
FIG. 12 is a Southern Blot of amplified Brucella omp2 DNA hybridized with the diagnostic probe 2b.

Aliquots of Brucella DNA prepared for Example 1 were treated as described in Example 1, but digested with Pst I in Pst I restriction enzyme buffer (as provided by the manufacturer, Boeringer- Mannheim). Electrophoresis and Southern blot analysis were carried out as described for Example 1. The results of the Southern Blot analysis are shown in FIG. 6, and indicate that the genetic variation of the omp2 locus segregated along classical species lines, that is the Pst I restriction fragment profiles of the omp2 gene locus were distinct for different species and Biovars of Brucella. Based on Pst I restriction digestion, the species can be divided into six groups as shown in FIG. 1. Group 1 includes *B. abortus* biovars 1, 2 and 4. Group 2 includes *B. abortus* biovars 3, 5, 6, 7 and 9. Group 3 includes only *B. melitensis*. Group 4 includes *B. suis* and *B. neotomae*. Additional restriction digestion with the restriction enzyme Kpn I enabled distinction of Group 5, *B. canis* from the species of Group 4. Group 6 contains only *B. ovis*.

This data indicates that after one restriction digest with Pst I, analysis of the restriction fragments can distinguish between *B. abortus*, *B. ovis*, *B. melitensis*, and the remaining species of Brucella. Restriction fragments generated from Pst1 digestion can also distinguish between *B. abortus* biovars 1, 2 and 4 from *B. abortus* biovars 3, 5, 6, 7 and 9. Additional digestion with Kpn I permits the distinctive identification of *B. canis*.

EXAMPLE 3

Detection of Brucella in Tissue Samples of Infected and Control Cattle by Amplification of omp2 DNA Cattle (two) (mixed breed, (*Bos Taurus* × *Bos Indicus*, Montana Beaver Head Ranch, Big Hole, Mont.), at approximately 120 days gestation, were infected with 1×10⁷ *B. abortus* S2308 organisms (obtained from Dr. Billy Deyoe, U.S.D.A. N.A.D.C.). Abomasal tissue samples were prepared from either aborted calves or live calves of the two infected animals and two noninfected control animals.

Abomasal tissue samples were obtained by necroscopy following animal sacrifice. The fetal stomach or abomasum and its contents were dissected and stored in whirlpak bags (NASCO, Fort Atkinson, Wis.). Portions of the abomasal samples were heated at 68° C. for 2 hours in eppendorf tubes to kill any live Brucella, and 5 μl portions were then added to amplification reactions according to the method of Saiki et al, 1985.

The standard amplification reaction was performed in a final volume of 100 μl containing 200 μM of each nucleotide (dNTP, dGTP, dCTP, dTTP), 2.5 units Taq polymerase, approximately 0.1 ng template DNA and 1 μM each oligonucleotide primer. The reaction buffer also contained 10 mM TRIS-HCl, pH 8.3, 50 mM KCl, 1.5 mM $MgCl_2$, and 0.01% w/v gelatin. The oligonucleotides used to prime the amplification were No. 32 and No. 33, as shown in Table 2, which amplified the omp2b gene of Brucella.

The DNA was amplified through 30 cycles including a 30 second melting at 94° C., annealing over 30 seconds at 62°-65° C., and polymerization at 72° C. for three minutes.

The amplified DNA was then sized in a 1-2% w/v agarose gel and stained with ethidium bromide to visualize the DNA. As shown in FIG. 7, DNA obtained from infected animals amplified the 1268 bp omp2b gene fragment characteristic of Brucella. Non-infected animals showed no amplified DNA product.

EXAMPLE 4

Detection of Brucella in Milk Samples From Infected and Control Cattle

Pregnant cattle (six) (*Bos Taurus*×*Bos Indicus*, Montana Beaver Head Ranch, Big Hole, Mont.), at approximately 120 days gestation were infected with $1\times10^7$ *B. abortus* S2308 (obtained from Dr. Billy Deyoe) organisms by conjunctival installation. Four uninfected cattle served as controls. The animals are monitored serologically for infection until abortion or the birth of a live calf. Samples collected for bacteriologic analysis are used for PCR amplification and DNA analysis of Brucella.

Blood samples are collected weekly; sera is tested by the following methods:

1. buffered Brucella antigen (Card) (O'Reilly and Cunningham, 1971, *Vet. Rec.* 88: 590-594; Ladwig, 1968, *Iowa Vet.* 39: 9-14).
2. enzyme linked immunosorbent assay (ELIZA) (Heck et al, 1980, *Am. J. Vet. Res.* 41: 2082-2084).
3. rivanol precipitation plate agglutination (Huber and Nicoletti, 1986, *Am. J. Vet. Res.* 47: 1529-1531).
4. automated tube (warm) complement fixation with Brucella antigens and hemolysis in gel test (Timbs et al, 1978, *N.Z. Vet. J.* 26: 52-56; Nicoletti and Carlsen, 1981, *Am. J. Vet. Res.* 42: 1494-1497).

Vaginal and rectal swabs, placental and quarter milk samples from all parturient cattle will be cultured for Brucella. Rectal swabs from viable calves, and pulmonary tissue, gastric contents, mediastinal lymph nodes, and rectal swabs from dead fetuses or neonates will be streaked onto semi-restrictive Brucella agar medium with 5% bovine serum and antibiotics (Farrell's Medium, Farrell et al, 1974, *Res. Vet. Sci.* 16: 280-286).

Culture negative parturient principals and controls will be euthanized and at least 50 tissues will be collected, trimmed of non-lymphatic tissue, and both sides of the cut surface will be rubbed over the surfaces of Farrell's media (3 plates per tissue sample). Inoculated media will be incubated at least 7 days at 37° C. in 10% $CO_2$ with bacterial colonies resembling Brucella further identified and biotyped by conventional methods for comparison with results for the same animal from PCR amplification and analysis of DNA from tissue and fluid samples.

DNA obtained from blood, milk, semen, vaginal secretions, rectal secretions and tissue samples will be concentrated if necessary onto nitrocellulose filters. The DNA obtained will be amplified according to the procedure described for Example 3, using oligonucleotides which amplify specific regions of the omp2 gene locus. Amplification of the omp2b gene locus and identification of the omp2b gene as described for Example 3 will identify the presence of Brucella organisms. Amplification of the omp2a gene using the oligonucleotides No. 34 and No. 35, as shown in Table 2, followed by electrophoretic analysis of the amplified sequence will be used to determine the presence of Brucella in the test sample. Restriction digestion of the amplified DNA sequence using the enzyme Pst I will characterize the infecting Brucella species as *B. abortus* biovars 1, 2, 4, *B. abortus* biovars 3, 5, 6, 9. *B. ovis, B. melitensis*, or one of the remaining three Brucella species. Restriction digestion using the enzyme Kpn I will distinguish *B. canis* from the remaining two Brucella species, *B. suis* and *B. neotomae*.

EXAMPLE 5

Identification of Brucella Species and Biovars Using Specific Hydridization Probes DNA was extracted by from each of the known Brucella species and from *B. abortus* biovars 1 and 5. A diagnostic region of the omp2 gene locus was PCR amplified using amplification primers having Seq. ID Nos. 19 and 20. Cells were added to a standard PCR reaction mix containing 1 X reaction buffer (10 mM Tris-HCl, pH 8.3/50 mM KCl), 1.5 mM $MgCl_2$ 200 μM of each dNTP, 0.2 μM of each primer and 1 unit of Taq or Tth polymerases. Amplification primers (Seq. Id Nos. 19 and 20) were added to initiate the reactions during a hot start preincubation step at 84° C. This was followed by an initial 94° C. heating prior to thermal cycling. Standard reaction conditions can also be employed using 94° C. melting, 50° C. annealing, and 72° C. polymerization. The products of these reactions were electrophoresed on a 1.5% agarose gels and transferred to nylon membranes. The nylon filter was prehybridized overnight at 68° C. for 16-24 hours in 50 ml prehybridization buffer (6XSSPE, 0.1% (w/v) NaPPi, 0.1% (w/v) SDS, 0.5% (w/v) blotto, 0.1 mg/ml ssDNA, and 0.02 mg/ml *E. coli* tRNA).

Oligonucleotides were labeled by mixing the following:

| | |
|---|---|
| α[$^{32}$P]-ATP (6000 Ci/mmol) | 100 μCi |
| oligonucleotide (20 μg/ml) | 1 μl |
| 5X Tailing buffer (Boehringer Mannheim) | 3 μl |
| $CoCl_2$ | 4.5 μl |
| TdT (55 units/μl) | 1 μl |

|        |           |
|--------|-----------|
| -continued |       |
| dH₂O   | to 15 μl  |

The mixture was incubated at 37° C. for 30 minutes. The labeled oligonucleotides (25/200 μl) were passed over a G-25 column and placed in 4 ml 6XSSPE containing 0.1% (w/v) SDS.

The filter containing the amplified DNA was hybridized in the labeled oligonucleotide solution overnight usually at 37° C. but no more than $T_m-5°$ C., which was calculated from the following formula: $Tm=4(G+C)+2(A+T)$. After hybridization, the filter was washed 4 X at room temperature in 6XSSPE containing 0.1% (w/v) SDS, and at the appropriate temperature (depending on the desired stringency), blotted dry, wrapped in Saran wrap and exposed to X-ray film.

Amplified DNA from each Brucella species and biovar was hybridized with diagnostic oligonucleotide probes 1(a-c) and 2(a,b), at stringencies of 37, 50, 60, and 66° C. The resulting blots are shown in FIGS. 8–12, and the pattern of specific probe hybridization is shown in Table 6.

TABLE 6

|              | 1 | | | 2 | |
|--------------|---|---|---|---|---|
|              | a | b | c | a | b |
| *B. biovar 5*   | + | − | − | + | − |
| *B. melitensis* | + | − | − | + | − |
| *B. suis*       | + | − | − | − | + |
| *B. canis*      | + | − | − | − | + |
| *B. neotomae*   | − | + | − | + | − |

Having described the invention above, various modifications of the techniques, procedures, materials, and equipment will be apparent to those in the art. It is intended that all such variations within the scope and spirit of the appended claims be embraced thereby.

We claim:

1. A method for identifying a species or biovar of Brucella comprising the steps of:
 releasing DNA from a test sample;
 amplifying a gene sequence of a Brucella omp2 gene locus as defined in FIGS. 2A-O from the released DNA, said gene sequence having sufficient diversity to distinguish species of Brucella;
 analyzing the hybridization of the amplified gene sequence with a panel of DNA probes to identify a species or biovar of Brucella.

2. The method of claim 1 wherein said amplified gene sequence is a sequence between nucleotides 2470 and 3346 of the Brucella omp2 gene consensus sequence.

3. The method of claim 1 wherein said amplifying is by polymerase chain reaction.

4. The method of claim 3, wherein the polymerase chain reaction is primed with an oligonucleotide pair which anneals to the omp2 gene locus of Brucella to amplify a sequence between nucleotides 2470 and 3346 of the Brucella omp2 consensus sequence.

5. The method of claim 3, wherein the polymerase chain reaction is primed with an oligonucleotide pair selected from those having Seq. Id. Nos. 9-20.

6. The method of claim 4, wherein said oligonucleotide pair is that having Seq. Id. Nos. 19 and 20.

7. The method of claim 6, wherein said panel of DNA probes includes one or more of the probes having Seq. Id. Nos. 21-32.

8. The method of claim 7, wherein said panel includes at least two probes having Seq. Id. Nos. 21-32.

9. The method of claim 1, wherein said test sample is animal fluid or tissue.

10. The method of claim 7 wherein said test sample is urine, blood, milk, semen, vaginal or rectal secretions.

11. The method of claim 8, wherein said test sample is milk.

12. The method of claim 1, wherein said analyzing is by dot blot, DNA hybridization, or by agarose gel electrophoresis.

13. The method of claim 12, wherein said analyzing is using radiolabeled oligonucleotide probes.

* * * * *

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 3378 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| CAGGCGATCT | TCCGCGACCC | CTGTAGAAAG | ACTGCGGTCA | GCATAAAAAG | CAAGCATCTG | 60 |
| ATGCTGCACG | AGGGCAACAA | AAAACCCGGY | ATTTCTGCCG | GGTTTCTGTA | TCCAATCCGT | 120 |
| AATGGATTAG | AACGAACGCT | GGAAGCGAAC | GATACCGCCC | CAAGCATTGT | CTTCAGCAAC | 180 |
| RGTGTTCTTC | CACTCGCCAC | CAAACTTGGT | GTAGGAAACT | TCCGGMGYAA | CGGTGAAGCC | 240 |
| AGGAACCAGT | TCGTAAGCAA | CGTTAGCCGT | AACTGCCGTC | TTGCCCCAGT | CGTCATGCGC | 300 |
| AGCCTGCAGR | TTGAAGGYWG | CCTTYTSSGT | RGCMWKRWAC | TTYRSACCAC | CCCAGACAGC | 360 |
| CCAATCGCCG | CCCCACTGRC | CGTAGTTCTG | RTYCGGCGTM | GCWGCGGACG | AATATGCGCC | 420 |
| CTGCARCCAW | ACCGAGAACY | GGTCGGTGAT | GTTGACGTCG | CCACGAACCT | TKGYAGCCCA | 480 |
| TTCTTCKATG | ACCGAGTCAT | AGGCAACAAC | ACCAGCGATC | GAACCCCAGC | CGCCAGCATA | 540 |
| YTTCAGGCCG | CCAACAACGT | SMGGCATGTA | RCCGTCGATS | BKGTARTYGG | TCGTGCCAGT | 600 |
| GTAAYYRYCR | WCGTYKTCGC | CACCCTGTTC | GAGAGCGATC | ACAGCCGAGA | AGCCGTTTCC | 660 |
| GCCRGTGAAG | GTGTASGMGA | TCTTGCCGGT | GCGGTAGGAG | CCAGCCGAGA | TCACGTCATC | 720 |
| GTTGATGAYA | TCRCCGAGGT | AACCGGTGAA | GGTATGGAAT | TCSGATTCRT | CGATACCAAC | 780 |
| SYKSARACCA | CCRAGCKKGA | TATAYGCRAA | CTSCAKRWCG | GTGCCGSTGC | TTACGCTGCC | 840 |
| ATCAGCGACA | TCACGATCAT | CGSTKWMATY | RCCRTATTKR | CCATCWWSRC | SYGAATTGTT | 900 |
| SSYRGYRTAG | TTGAAGCGCA | GYKYRGTRWA | GGTSYYGAGK | GTGCCGAGTT | CGGTTTCCGA | 960 |
| AYYSGTGTKR | AACRYGGAGT | GCRAACGAG | CRCYCTTGTC | CCAGCCWTTR | CGRTCSGWRC | 1020 |
| CGGWRTAAAC | GTCRTCGCCG | CCCTTTACGT | CGTAACGGAC | GTARCCRYKG | AYGCGCAGGC | 1080 |
| AGGTTTCGGT | GCCCGGAATG | TAGAAGTAGC | CAGCGCCRTA | AGCGTCGCAA | ACGCGGACAT | 1140 |

-continued

```
ATTCAACGGC TTCGGGCTCT GGCGCGACGA TTGCGTCGGC AGCYTGAGCG CCGGAAGCTG    1200
CAACCAGAGC TGCAGCGGAG CCAAGGAGAA GGCTCTTGAT GTTCATTTCT GACCTCCAGT    1260
CAAAGTTAAA AATGGGTCTR GGCATTCTGA TTTGGCTGAA GGACAACCTG TCCCCATCCC    1320
CTAATTGAAA AAGTCGCCCC GAAGCGCTCC TTCTTCTGAA AGTGAAGATA CTCGCCCATT    1380
TATTCGTTTC AACATCGAAT ATGTTCTCAC AACCTTTAYG GTGCTGCTAT GAAGGGCAGT    1440
TRTTGCWGAA ATGACACRAA ATTACCTGCT TTAGCTCGGC GGATTCATGC TTTATTAACA    1500
TAAGTRAACG CGAATTAACC GATGTTAACG TTTGAAAATG CAAGTTTTTT AGGATCGCCT    1560
RCMGAATAAA GCCGCRRATC TTTCGTCGAA ACAGCCCTTA ACGGAATATG TCGGCAAGGT    1620
GGCAAGAATC GTCTGAACGG AGAGCAGAAA CCTCGAATCC GTTTCATTTA ATAAGGGCAA    1680
GTGCGTGCCG GTGCTAAATT GTGGGCCTTT TTAAGCGCGC YATATATATA AAGAGAATAA    1740
TCCGCAGGAA ATTTTACCAG TTAATGCGTA AATCGCTTGA AATGCCCAGG CGTACCGGTT    1800
ATCTCGCCTT TACCGGAGAG GTGGCCGAGT GGTCGAAGGC GCTCCCTGC TAAGGGAGTA    1860
GACCTCAAAA GGGTCTCGTG GGTTCGAATC CCATCCTCTC CGCCAGTTTT TCCAATATCC    1920
CAGCAAATCT TTATGTGTTC GACGCGCTTG ATTTCATACG GAATCGGCTT TTACCCCTCG    1980
CGCACTGAAT CTCTGTTTTT CCAGGCTACG AATCCAGAAA ACAAGCAAGC CATTGATAAG    2040
TAATGGCTAT TCAAAATTCT GGCRATTCTT GACTGGAGGT CAGAAATGAA CATCAAGAGC    2100
CTTCTCCTTG GCTCCGCYGC AGCTCTGGTT GCAGCTTCCG GCGCTCARGC TGCCGACGCA    2160
ATCGTCGCGC CRGAGCCCGA AGCCGTTGAA TATGTCCGCG TTTGCGACGC TTAYGGCGCT    2220
GGCTACTTCT ACATTCCGGG CACCGAAACC TGCCTGCGCR TCMRYGGYTA CGTCCGTTAC    2280
GACGTAAAGG GCGGCGAYGA CGTTTAYWCC GGYWCSGAYC GYAAWGGCTG GACAAGGGY    2340
GCTCGTTTYG CACTCATGTT CAACACGAAT TCGGAAACCG AACTCGGCAC ACTCGGCACC    2400
TATACTCAGC TGCGCTTCAA CTACACCAGC AACAATTCAC GTCATGATGG CCAATACGGC    2460
GATTTCAGCG ATGATCGTGA TGTCGCTGAT GGCRGCGTAA GCACCGGCAC CGATCTGCAG    2520
TTTGCATATA TCACGCTTGG TGGTTTCAAG GTTGGTATCG ACGAATCCGA ATTCCATACC    2580
TTCACCGGTT ACCTCGGTGA TRTCATCAAC GATGAYGTSR TCKCKGMTGG CTCCTACCGC    2640
ACCGGCAAGA TCGCCTACAC CTTCACCGGC GGAAACGGCT TCYCGGCTGT GATCGCTCTC    2700
GAACAGGGTG GCGAAGACGT TGACAACGAT TACACGATCG ACGGTTACAT GCCGCACGTT    2760
GTTGGCGGCC TGAAATATGC TGGCGGCTGG GGTTCGATCG CTGGTGYTGT TGCCTATGAC    2820
YCGGTCATCG AAGAATGGGC TACAAAGGTT CGTGGCGACG TCAACATCAC CGACCGGTTC    2880
TCGGTATGGC TGCAGGGCGC ATATTCGTCC GCAGCGACGC CGAACCAGAA CTACGGTCAG    2940
TGGGGCGGCG ATTGGGCTGT CTGGGGTGGT GCAAAGTTCA TTGCCMCCGA AAAGGYAACC    3000
TTCAATCTGC AGGCTGCGCA TGACGACTGG GGCAAGACSG CAGTTACSGC YAACGTYGCT    3060
TAYSARCTSG TTCCYGGMTT CACCRTTACG CCGGAAGTTT CCTACACCAA ATTTGGTGGC    3120
GAGTRGAAAG ACACCGTTGC TGAAGACAAT GCCTGGGGCG GTATCGTTCS YTTCCAGCGC    3180
TCGTTCTAAT CAGATCGACG TTAAGCATAG GGCGCCAACG GTTTCCCGTT GGCGCCGGTT    3240
CATTTGAAAC AGCGTTCACG AAAGCGTGAG AATCGATTCT TCCGGAATGG GGATTCCAGG    3300
CGGATCGACA ATTGAGGGAA TTGCGGGGAC GACAAAAAGC TGGGGGCAAC CGGGGGGTCT    3360
TGTAAAGGAT TGAGCCAM                                                  3378
```

( 2 ) INFORMATION FOR SEQ ID NO:2:

( i ) SEQUENCE CHARACTERISTICS:
  ( A ) LENGTH: 3347 base pairs
  ( B ) TYPE: nucleic acid -continued ( C ) STRANDEDNESS: single
( D ) TOPOLOGY: linear ( i i ) MOLECULE TYPE: cDNA ( v i ) ORIGINAL SOURCE:
( A ) ORGANISM: Brucella abortus
( B ) STRAIN: biovar 5

( x i ) SEQUENCE DESCRIPTION: SEQ ID NO:2:

```
CAGGCGATCT TCCGCGACCC CTGTAGAAAG ACTGCGGTCA GCATAAAAAG CAAGCATCTG 60

ATGCTGCACG AGGGCAACAA AAAACCCGGC ATTTCTGCCG GGTTTCTGTA TCCAATCCGT 120

AATGGATTAG AACGAACGCT GGAAGCGAAC GATACCGCCC CAAGCATTGT CTTCAGCAAC 180

GGTGTTCTTC CACTCGCCAC CAAACTTGGT GTAGGAAACT TCCGGCGTAA CGGTGAAGCC 240

AGGAACCAGT TCGTAAGCAA CGTTAGCCGT AACTGCCGTC TTGCCCCAGT CGTCATGCGC 300

AGCCTGCAGG TTGAAGGCAG CCTTCTGCGT AGCCTGATAC TTCAGACCAC CCCAGACAGC 360

CCAATCGCCG CCCCACTGGC CGTAGTTCTG ATCCGGCGTA GCAGCGGACG AATATGCGCC 420

CTGCAACCAA ACCGAGAACT GGTCGGTGAT GTTGACGTCG CCACGAACCT TGGCAGCCCA 480

TTCTTCGATG ACCGAGTCAT AGGCAACAAC ACCAGCGATC GAACCCCAGC CGCCAGCATA 540

CTTCAGGCCG CCAACAACGT CAGGCATGTA GCCGTCGATG TGGTAGTTGG TCGTGCCAGT 600

GTAACCACCG TCGTTGTCGC CACCCTGTTC GAGAGCGATC ACAGCCGAGA AGCCGTTTCC 660

GCCAGTGAAG GTGTACGAGA TCTTGCCGGT GCGGTAGGAG CCAGCCGAGA TCACGTCATC 720

GTTGATGACA TCGCCGAGGT AACCGGTGAA GGTATGGAAT TCCGATTCAT CGATACCAAC 780

GCGCAGACCA CCGAGCTGGA TATACGCGAA CTCCATGACG GTGCCGCTGC TGGTTTCATT 840

ACCATATTTA CCATCTACGC CCGAATTGTT CGCAGCATAG TTGAAGCGCA GTTCGGTGAA 900

GGTCTTGAGG GTGCCGAGTT CGGTTTCCGA ACCGGTGGAA ACGCGGAGTG CGAAACGAGC 960

GCTCTTGTCC CAGCCATTGC GGTCGGTACC GGAGTAAACG TCATCGCCGC CCTTTACGTC 1020

GTAACGGACG TAACCATGGA CGCGCAGGCA GGTTTCGGTG CCCGGAATGT AGAAGTAGCC 1080

AGCGCCGTAA GCGTCGCAAA CGCGGACATA TTCAACGGCT TCGGGCTCTG GCGCGACGAT 1140

TGCGTCGGCA GCCTGAGCGC CGGAAGCTGC AACCAGAGCT GCAGCGGAGC CAAGGAGAAG 1200

GCTCTTGATG TTCATTTCTG ACCTCCAGTC AAAGTTAAAA ATGGGTCTGG GCATTCTGAT 1260

TTGGCTGAAG GACAACCTGT CCCCATCCCC TAATTGAAAA AGTCGCCCCG AAGCGCTCCT 1320

TCTTCTGAAA GTGAAGATAC TCGCCCATTT ATTCGTTTCA ACATCGAATA TGTTCTCACA 1380

ACCTTTATGG TGCTGCTATG AAGGGCAGTT GTTGCAGAAA TGACACGAAA TTACCTGCTT 1440

TAGCTCGGCG GATTCATGCT TTATTAACAT AAGTGAACGC GAATTAACCG ATGTTAACGT 1500

TTGAAAATGC AAGTTTTTTA GGATCGCCTG CAGAATAAAG CCGCGAATCT TTCGTCGAAA 1560

CAGCCCTTAA CGGAATATGT CGGCAAGGTG GCAAGAATCG TCTGAACGGA GAGCAGAAAC 1620

CTCGAATCCG TTTCATTTAA TAAGGGCAAG TGCGTGCCGG TGCTAAATTG TGGGCCTTTT 1680

TAAGCGCGCC ATATATATAA AGAGAATAAT CCGCAGGAAA TTTTACCAGT TAATGCGTAA 1740

ATCGCTTGAA ATGCCCAGGC GTACCGGTTA TCTCGCCTTT ACCGGAGAGG TGGCCGAGTG 1800

GTCGAAGGCG CTCCCCTGCT AAGGGAGTAG ACCTCAAAAG GGTCTCGTGG GTTCGAATCC 1860

CATCCTCTCC GCCAGTTTTT CCAATATCCC AGCAAATCTT TATGTGTTCG ACGCGCTTGA 1920

TTTCATACGG AATCGGCTTT TACCCCTCGC GCACTGAATC TCTGTTTTTC CAGGCTACGA 1980

ATCCAGAAAA CAAGCAAGCC ATTGATAAGT AATGGCTATT CAAAATTCTG GCGATTCTTG 2040

ACTGGAGGTC AGAAATGAAC ATCAAGAGCC TTCTCCTTGG CTCCGCTGCA GCTCTGGTTG 2100

CAGCTTCCGG CGCTCAGGCT GCCGACGCAA TCGTCGCGCC AGAGCCCGAA GCCGTTGAAT 2160

-continued

```
ATGTCCGCGT TTGCGACGCT TACGGCGCTG GCTACTTCTA CATTCCGGGC ACCGAAACCT    2220
GCCTGCGCGT CCATGGTTAC GTCCGTTACG ACGTAAAGGG CGGCGATGAC GTTACTCCG    2280
GTACCGACCG CAATGGCTGG GACAAGGGCG CTCGTTTCGC ACTCATGTTC AACACGAATT    2340
CGGAAACCGA ACTCGGCACA CTCGGCACCT ATACTCAGCT GCGCTTCAAC TACACCAGCA    2400
ACAATTCACG TCATGATGGC CAATACGGCG ATTTCAGCGA TGATCGTGAT GTCGCTGATG    2460
GCGGCGTAAG CACCGGCACC GATCTGCAGT TTGCATATAT CACGCTTGGT GGTTTCAAGG    2520
TTGGTATCGA CGAATCCGAA TTCCATACCT TCACCGGTTA CCTCGGTGAT GTCATCAACG    2580
ATGATGTCGT CGCTGCTGGC TCCTACCGCA CCGGCAAGAT CGCCTACACC TTCACCGGCG    2640
GAAACGGCTT CTCGGCTGTG ATCGCTCTCG AACAGGGTGG CGAAGACGTT GACAACGATT    2700
ACACGATCGA CGGTTACATG CCGCACGTTG TTGGCGGCCT GAAATATGCT GGCGGCTGGG    2760
GTTCGATCGC TGGTGTTGTT GCCTATGACT CGGTCATCGA AGAATGGGCT ACAAAGGTTC    2820
GTGGCGACGT CAACATCACC GACCGGTTCT CGGTATGGCT GCAGGGCGCA TATTCGTCCG    2880
CAGCGACGCC GAACCAGAAC TACGGTCAGT GGGGCGGCGA TTGGGCTGTC TGGGGTGGTG    2940
CAAAGTTCAT TGCCCCCGAA AAGGCAACCT TCAATCTGCA GGCTGCGCAT GACGACTGGG    3000
GCAAGACCGC AGTTACCGCC AACGTCGCTT ATCAGCTCGT TCCCGGATTC ACCATTACGC    3060
CGGAAGTTTC CTACACCAAA TTTGGTGGCG AGTGGAAAGA CACCGTTGCT GAAGACAATG    3120
CCTGGGGCGG TATCGTTCGC TTCCAGCGCT CGTTCTAATC AGATCGACGT TAAGCATAGG    3180
GCGCCAACGG TTTCCCGTTG GCGCCGGTTC ATTTGAAACA GCGTTCACGA AAGCGTGAGA    3240
ATCGATTCTT CCGGAATGGG GATTCCAGGC GGATCGACAA TTGAGGGAAT GCGGGGACG    3300
ACAAAAAGCT GGGGCAACC GGGGGGTCTT GTAAAGGATT GAGCCAA                  3347
```

( 2 ) INFORMATION FOR SEQ ID NO:3:

( i ) SEQUENCE CHARACTERISTICS:
        ( A ) LENGTH: 3208 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Brucella abortus
        ( B ) STRAIN: biovar 1 (S2308)

( x i ) SEQUENCE DESCRIPTION: SEQ ID NO:3:

```
CAGGCGATCT TCCGCGACCC CTGTAGAAAG ACTGCGGTCA GCATAAAAG CAAGCATCTG      60
ATGCTGCACG AGGGCAACAA AAAACCCGGC ATTTCTGCCG GGTTTCTGTA TCCAATCCGT    120
AATGGATTAG AACGAACGCT GGAAGCGAAC GATACCGCCC AAGCATTGT CTTCAGCAAC    180
GGTGTTCTTC CACTCGCCAC CAAACTTGGT GTAGGAAACT TCCGGCGTAA CGGTGAAGCC    240
AGGAACCAGT TCGTAAGCAA CGTTAGCCGT AACTGCCGTC TTGCCCAGT CGTCATGCGC    300
AGCCTGCAGG TTGAAGGCAG CCTTCTGCGT AGCCTGATAC TTCAGACCAC CCAGACAGC    360
CCAATCGCCG CCCCACTGGC CGTAGTTCTG ATCCGGCGTA GCAGCGGACG AATATGCGCC    420
CTGCAACCAA ACCGAGAACT GGTCGGTGAT GTTGACGTCG CCACGAACCT GGCAGCCCA    480
TTCTTCTATG ACCGAGTCAT AGGCAACAAC ACCAGCGATC GAACCCCAGC CGCCAGCATA    540
CTTCAGGCCG CCAACAACGT CAGGCATGTA GCCGTCGATG TGGTAGTTGG TCGTGCCAGT    600
GTAACCACCG TCGTTGTCGC CACCCTGTTC GAGAGCGATC ACAGCCGAGA AGCCGTTTCC    660
GCCAGTGAAG GTGTACGAGA TCTTGCCGGT GCGGTAGGAG CCAGCCGAGA TCACGTCATC    720
```

```
GTTGATGACA TCGCCGAGGT AACCGGTGAA GGTATGGAAT TCCGATTCAT CGATACCAAC      780
GCGCAGACCA CCGAGCTGGA TATACGCGAA CTCCATGACG GTGCCGCTGC TGGTTTCATT      840
ACCATATTTA CCATCTACGC CCGAATTGTT CGCAGCATAG TTGAAGCGCA GTTCGGTGAA      900
GGTCTTGAGG GTGCCGAGTT CGGTTTCCGA ACCGGTGGAA ACGCGGAGTG CGAAACGAGC      960
GCTCTTGTCC CAGCCATTGC GGTCGGTACC GGAGTAAACG TCATCGCCGC CCTTTACGTC     1020
GTAACGGACG TAACCATGGA CGCGCAGGCA GGTTTCGGTG CCCGGAATGT AGAAGTAGCC     1080
AGCGCCGTAA GCGTCGCAAA CGCGGACATA TTCAACGGCT TCGGGCTCTG GCGCGACGAT     1140
TGCGTCGGCA GCCTGAGCGC CGGAAGCTGC AACCAGAGCT GCAGCGGAGC CAAGGAGAAG     1200
GCTCTTGATG TTCATTTCTG ACCTCCAGTC AAAGTAAAAA ATGGGTCTGG CATTCTGAT      1260
TTGGCTGAAG GACAACCTGT CCCCATCCCC TAATTGAAAA AGTCGCCCCG AAGCGCTCCT     1320
TCTTCTGAAA GTGAAGATAC TCGCCCATTT ATTCGTTTCA ACATCGAATA TGTTCTCACA     1380
ACCTTTATGG TGCTGCTATG AAGGGCAGTT GTTGCAGAAA TGACACGAAA TTACCTGCTT     1440
TAGCTCGGCG GATTCATGCT TTATTAACAT AAGTGAACGC GAATTAACCG ATGTTAACGT     1500
TTGAAAATGC AAGTTTTTA GGATCGCCTG CAGAATAAAG CCGCGAATCT TTCGTCGAAA      1560
CAGCCCTTAA CGGAATATGT CGGCAAGGTG GCAAGAATCG TCTGAACGGA GAGCAGAAAC     1620
CTCGAATCCG TTTCATTTAA TAAGGGCAAG TGCGTGCCGG TGCTAAATTG TGGGCCTTTT     1680
TAAGCGCGCC ATATATATAA AGAGAATAAT CCGCAGGAAA TTTTACCAGT TAATGCGTAA     1740
ATCGCTTGAA ATGCCCAGGC GTACCGGTTA TCTCGCCTTT ACCGGAGAGG TGGCCGAGTG     1800
GTCGAAGGCG CTCCCCTGCT AAGGGAGTAG ACCTCAAAAG GGTCTCGTGG GTTCGAATCC     1860
CATCCTCTCC GCCAGTTTTT CCAATATCCC AGCAAATCTT TATGTGTTCG ACGCGCTTGA     1920
TTTCATACGG AATCGGCTTT TACCCCTCGC GCACTGAATC TCTGTTTTTC CAGGCTACGA     1980
ATCCAGAAAA CAAGCAAGCC ATTGATAAGT AATGGCTATT CAAAATTCTG GCGATTCTTG     2040
ACTGGAGGTC AGAAATGAAC ATCAAGAGCC TTCTCCTTGG CTCCGCTGCA GCTCTGGTTG     2100
CAGCTTCCGG CGCTCAGGCT GCCGACGCAA TCGTCGCGCC AGAGCCCGAA GCCGTTGAAT     2160
ATGTCCGCGT TTGCGACGCT TACGGCGCTG GCTACTTCTA CATTCCGGGC ACCGAAACCT     2220
GCCTGCGCGT CCATGGTTAC GTCCGTTACG ACGTAAAGGG CGGCGATGAC GTTTACTCCG     2280
GTACCGACCG CAATGGCTGG GACAAGGGCG CTCGTTTCGC ACTCATGTTC AACACGAATT     2340
CGGAAACCGA ACTCGGCACA CTCGGCACCT ATACTCAGCT GCGCTTCAAC TACACCAGCA     2400
ACAATTCACG TCATGATGGC CAATACGGCG ATTTCAGCGA TGATCGTGAT GTCGCTGATG     2460
GCGGCGTAAG CACCGGCAAG ATCGCCTACA CCTTCACCGG CGGAAACGGC TTCTCGGCTG     2520
TGATCGCTCT CGAACAGGGT GGCGAAGACG TTGACAACGA TTACGATC GACGGTTACA       2580
TGCCGCACGT TGTTGGCGGC CTGAAATATG CTGGCGGCTG GGGTTCGATC GCTGGTGTTG     2640
TTGCCTATGA CTCGGTCATC GAAGAATGGG CTACAAAGGT TCGTGGCGAC GTCAACATCA     2700
CCGACCGGTT CTCGGTATGG CTGCAGGGCG CATATTCGTC CGCAGCGACG CCGAACCAGA     2760
ACTACGGTCA GTGGGGCGGC GATTGGGCTG TCTGGGGTGG TGCAAAGTTC ATTGCCCCCG     2820
AAAAGGCAAC CTTCAATCTG CAGGCTGCGC ATGACGACTG GGCAAGACC GCAGTTACCG      2880
CCAACGTCGC TTATCAGCTC GTTCCCGGAT TCACCATTAC GCCGGAAGTT TCCTACACCA     2940
AATTTGGTGG CGAGTGGAAA GACACCGTTG CTGAAGACAA TGCCTGGGGC GGTATCGTTC     3000
GCTTCCAGCG CTCGTTCTAA TCAGATCGAC GTTAAGCATA GGGCGCCAAC GGTTTCCCGT     3060
TGGCGCCGGT TCATTTGAAA CAGCGTTCAC GAAAGCGTGA GAATCGATTC TTCCGGAATG     3120
GGGATTCCAG GCGGATCGAC AATTGAGGGA ATTGCGGGGA CGACAAAAAG CTGGGGGCAA     3180
```

CCGGGGGGTC TTGTAAAGGA TTGAGCCA 3208

(2) INFORMATION FOR SEQ ID NO:4:

(i) SEQUENCE CHARACTERISTICS:
        (A) LENGTH: 3346 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Brucella canis (xi) SEQUENCE DESCRIPTION: SEQ ID NO:4:

```

```
TTTCATACGG AATCGGCTTT TACCCCTCGC GCACTGAATC TCTGTTTTTC CAGGCTACGA    1980

ATCCAGAAAA CAAGCAAGCC ATTGATAAGT AATGGCTATT CAAAATTCTG GCGATTCTTG    2040

ACTGGAGGTC AGAAATGAAC ATCAAGAGCC TTCTCCTTGG CTCCGCTGCA GCTCTGGTTG    2100

CAGCTTCCGG CGCTCAGGCT GCCGACGCAA TCGTCGCGCC AGAGCCCGAA GCCGTTGAAT    2160

ATGTCCGCGT TTGCGACGCT TACGGCGCTG GCTACTTCTA CATTCCGGGC ACCGAAACCT    2220

GCCTGCGCGT CCATGGTTAC GTCCGTTACG ACGTAAAGGG CGGCGACGAC GTTTATACCG    2280

GCTCGGATCG TAAAGGCTGG GACAAGGGCG CTCGTTTCGC ACTCATGTTC AACACGAATT    2340

CGGAAACCGA ACTCGGCACA CTCGGCACCT ATACTCAGCT GCGCTTCAAC TACACCAGCA    2400

ACAATTCACG TCATGATGGC CAATACGGCG ATTTCAGCGA TGATCGTGAT GTCGCTGATG    2460

GCGGCGTAAG CACCGGCACC GATCTGCAGT TTGCATATAT CACGCTTGGT GGTTTCAAGG    2520

TTGGTATCGA CGAATCCGAA TTCCATACCT TCACCGGTTA CCTCGGTGAT GTCATCAACG    2580

ATGATGTCGT CGCTGCTGGC TCCTACCGCA CCGGCAAGAT CGCCTACACC TTCACCGGCG    2640

GAAACGGCTT CTCGGCTGTG ATCGCTCTCG AACAGGGTGG CGAAGACGTT GACAACGATT    2700

ACACGATCGA CGGTTACATG CCGCACGTTG TTGGCGGCCT GAAATATGCT GGCGGCTGGG    2760

GTTCGATCGC TGGTGCTGTT GCCTATGACC CGGTCATCGA AGAATGGGCT ACAAAGGTTC    2820

GTGGCGACGT CAACATCACC GACCGGTTCT CGGTATGGCT GCAGGGCGCA TATTCGTCCG    2880

CAGCGACGCC GAACCAGAAC TACGGTCAGT GGGGCGGCGA TTGGGCTGTC TGGGGTGGTG    2940

CAAAGTTCAT TGCCACCGAA AAGGCAACCT TCAATCTGCA GGCTGCGCAT GACGACTGGG    3000

GCAAGACCGC AGTTACCGCC AACGTCGCTT ATCAGCTCGT TCCCGGATTC ACCATTACGC    3060

CGGAAGTTTC CTACACCAAA TTTGGTGGCG AGTGGAAAGA CACCGTTGCT GAAGACAATG    3120

CCTGGGGCGG TATCGTTCGC TTCCAGCGCT CGTTCTAATC AGATCGACGT TAAGCATAGG    3180

GCGCCAACGG TTTCCCGTTG GCGCCGGTTC ATTTGAAACA GCGTTCACGA AAGCGTGAGA    3240

ATCGATTCTT CCGGAATGGG GATTCCAGGC GGATCGACAA TTGAGGGAAT GCGGGGACG    3300

ACAAAAAGCT GGGGGCAACC GGGGGGTCTT GTAAAGGATT GAGCCA                   3346
```

( 2 ) INFORMATION FOR SEQ ID NO:5:

( i ) SEQUENCE CHARACTERISTICS:
        ( A ) LENGTH: 3346 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Brucella neotomae ( x i ) SEQUENCE DESCRIPTION: SEQ ID NO:5:

```
CAGGCGATCT TCCGCGACCC CTGTAGAAAG ACTGCGGTCA GCATAAAAAG CAAGCATCTG  60
ATGCTGCACG AGGGCAACAA AAAACCCGGC ATTTCTGCCG GGTTTCTGTA TCCAATCCGT  120
AATGGATTAG AACGAACGCT GGAAGCGAAC GATACCGCCC CAAGCATTGT CTTCAGCAAC  180
GGTGTTCTTC CACTCGCCAC CAAACTTGGT GTAGGAAACT TCCGGAGCAA CGGTGAAGCC  240
AGGAACCAGT TCGTAAGCAA CGTTAGCCGT AACTGCCGTC TTGCCCCAGT CGTCATGCGC  300
AGCCTGCAGA TTGAAGGTTG CCTTTTCGGT GGCAATGAAC TTTGCACCAC CCCAGACAGC  360
CCAATCGCCG CCCCACTGAC CGTAGTTCTG GTTCGGCGTC GCTGCGGACG AATATGCGCC  420
CTGCAACCAA ACCGAGAACT GGTCGGTGAT GTTGACGTCG CCACGAACCT TGGCAGCCCA  480
TTCTTCGATG ACCGAGTCAT AGGCAACAAC ACCAGCGATC GAACCCCAGC CGCCAGCATA  540
```

-continued

| | | | | | | |
|---|---|---|---|---|---|---|
| CTTCAGGCCG | CCAACAACGT | CAGGCATGTA | GCCGTCGATG | TGGTAGTTGG | TCGTGCCAGT | 600 |
| GTAACCACCG | TCGTTGTCGC | CACCCTGTTC | GAGAGCGATC | ACAGCCGAGA | AGCCGTTTCC | 660 |
| GCCAGTGAAG | GTGTACGAGA | TCTTGCCGGT | GCGGTAGGAG | CCAGCCGAGA | TCACGTCATC | 720 |
| GTTGATGACA | TCGCCGAGGT | AACCGGTGAA | GGTATGGAAT | TCCGATTCAT | CGATACCAAC | 780 |
| GCGCAGACCA | CCGAGCTGGA | TATACGCGAA | CTCCATGACG | GTGCCGCTGC | TGGTTTCATT | 840 |
| ACCATATTTA | CCATCTACGC | CCGAATTGTT | CGCAGCATAG | TTGAAGCGCA | GTTCGGTGAA | 900 |
| GGTCTTGAGG | GTGCCGAGTT | CGGTTTCCGA | ACCGGTGGAA | ACGCGGAGTG | CGAAACGAGC | 960 |
| GCTCTTGTCC | CAGCCATTGC | GGTCGGTACC | GGAGTAAACG | TCATCGCCGC | CCTTTACGTC | 1020 |
| GTAACGGACG | TAACCATGGA | CGCGCAGGCA | GGTTTCGGTG | CCCGGAATGT | AGAAGTAGCC | 1080 |
| AGCGCCGTAA | GCGTCGCAAA | CGCGGACATA | TTCAACGGCT | TCGGGCTCTG | GCGCGACGAT | 1140 |
| TGCGTCGGCA | GCCTGAGCGC | CGGAAGCTGC | AACCAGAGCT | GCAGCGGAGC | CAAGGAGAAG | 1200 |
| GCTCTTGATG | TTCATTTCTG | ACCTCCAGTC | AAAGTTAAAA | ATGGGTCTAG | GCATTCTGAT | 1260 |
| TTGGCTGAAG | GACAACCTGT | CCCCATCCCC | TAATTGAAAA | AGTCGCCCCG | AAGCGCTCCT | 1320 |
| TCTTCTGAAA | GTGAAGATAC | TCGCCCATTT | ATTCGTTTCA | ACATCGAATA | TGTTCTCACA | 1380 |
| ACCTTTACGG | TGCTGCTATG | AAGGGCAGTT | GTTGCAGAAA | TGACACGAAA | TTACCTGCTT | 1440 |
| TAGCTCGGCG | GATTCATGCT | TTATTAACAT | AAGTGAACGC | GAATTAACCG | ATGTTAACGT | 1500 |
| TTGAAAATGC | AAGTTTTTA | GGATCGCCTG | CCGAATAAAG | CCGCAAATCT | TTCGTCGAAA | 1560 |
| CAGCCCTTAA | CGGAATATGT | CGGCAAGGTG | GCAAGAATCG | TCTGAACGGA | GAGCAGAAAC | 1620 |
| CTCGAATCCG | TTTCATTTAA | TAAGGGCAAG | TGCGTGCCGG | TGCTAAATTG | TGGGCCTTTT | 1680 |
| TAAGCGCGCC | ATATATATAA | AGAGAATAAT | CCGCAGGAAA | TTTTACCAGT | TAATGCGTAA | 1740 |
| ATCGCTTGAA | ATGCCCAGGC | GTACCGGTTA | TCTCGCCTTT | ACCGGAGAGG | TGGCCGAGTG | 1800 |
| GTCGAAGGCG | CTCCCCTGCT | AAGGGAGTAG | ACCTCAAAAG | GGTCTCGTGG | GTTCGAATCC | 1860 |
| CATCCTCTCC | GCCAGTTTTT | CCAATATCCC | AGCAAATCTT | TATGTGTTCG | ACGCGCTTGA | 1920 |
| TTTCATACGG | AATCGGCTTT | TACCCCTCGC | GCACTGAATC | TCTGTTTTTC | CAGGCTACGA | 1980 |
| ATCCAGAAAA | CAAGCAAGCC | ATTGATAAGT | AATGGCTATT | CAAAATTCTG | GCGATTCTTG | 2040 |
| ACTGGAGGTC | AGAAATGAAC | ATCAAGAGCC | TTCTCCTTGG | CTCCGCTGCA | GCTCTGGTTG | 2100 |
| CAGCTTCCGG | CGCTCAGGCT | GCCGACGCAA | TCGTCGCGCC | GGAGCCCGAA | GCCGTTGAAT | 2160 |
| ATGTCCGCGT | TTGCGACGCT | TACGGCGCTG | GCTACTTCTA | CATTCCGGGC | ACCGAAACCT | 2220 |
| GCCTGCGCAT | CAGCGGCTAC | GTCCGTTACG | ACGTAAAGGG | CGGCGACGAC | GTTTATACCG | 2280 |
| GCTCGGATCG | TAAAGGCTGG | GACAAGGGCG | CTCGTTTCGC | ACTCATGTTC | AACACGAATT | 2340 |
| CGGAAACCGA | ACTCGGCACA | CTCGGCACCT | ATACTCAGCT | GCGCTTCAAC | TACACCAGCA | 2400 |
| ACAATTCACG | TCATGATGGC | CAATACGGCG | ATTTCAGCGA | TGATCGTGAT | GTCGCTGATG | 2460 |
| GCGGCGTAAG | CACCGGCACC | GATCTGCAGT | TTGCATATAT | CACGCTTGGT | GGTTTCAAGG | 2520 |
| TTGGTATCGA | CGAATCCGAA | TTCCATACCT | TCACCGGTTA | CCTCGGTGAT | GTCATCAACG | 2580 |
| ATGATGTCGT | CGCTGATGGC | TCCTACCGCA | CCGGCAAGAT | CGCCTACACC | TTCACCGGCG | 2640 |
| GAAACGGCTT | CCCGGCTGTG | ATCGCTCTCG | AACAGGGTGG | CGAAGACGTT | GACAACGATT | 2700 |
| ACACGATCGA | CGGTTACATG | CCGCACGTTG | TTGGCGGCCT | GAAATATGCT | GGCGGCTGGG | 2760 |
| GTTCGATCGC | TGGTGTTGTT | GCCTATGACT | CGGTCATCGA | AGAATGGGCT | ACAAAGGTTC | 2820 |
| GTGGCGACGT | CAACATCACC | GACCGGTTCT | CGGTATGGCT | GCAGGGCGCA | TATTCGTCCG | 2880 |
| CAGCGACGCC | GAACCAGAAC | TACGGTCAGT | GGGGCGGCGA | TTGGGCTGTC | TGGGGTGGTG | 2940 |
| CAAAGTTCAT | TGCCACCGAA | AAGGCAACCT | TCAATCTGCA | GGCTGCGCAT | GACGACTGGG | 3000 |

| | | | | | |
|---|---|---|---|---|---|
|GCAAGACGGC|AGTTACGGCT|AACGTTGCTT|ACGAACTGGT|TCCTGGCTTC|ACCGTTACGC|3060|
|CGGAAGTTTC|CTACACCAAA|TTTGGTGGCG|AGTGGAAAGA|CACCGTTGCT|GAAGACAATG|3120|
|CCTGGGGCGG|TATCGTTCGC|TTCCAGCGCT|CGTTCTAATC|AGATCGACGT|TAAGCATAGG|3180|
|GCGCCAACGG|TTTCCCGTTG|CGCCGGTTC|ATTTGAAACA|GCGTTCACGA|AAGCGTGAGA|3240|
|ATCGATTCTT|CCGGAATGGG|GATTCCAGGC|GGATCGACAA|TTGAGGGAAT|TGCGGGGACG|3300|
|ACAAAAAGCT|GGGGGCAACC|GGGGGGTCTT|GTAAAGGATT|GAGCCA| |3346|

( 2 ) INFORMATION FOR SEQ ID NO:6:

( i ) SEQUENCE CHARACTERISTICS:
        ( A ) LENGTH: 3361 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Brucella ovis ( x i ) SEQUENCE DESCRIPTION: SEQ ID NO:6:

| | | | | | |
|---|---|---|---|---|---|
|CAGGCGATCT|TCCGCGACCC|CTGTAGAAAG|ACTGCGGTCA|GCATAAAAAG|CAAGCATCTG|60|
|ATGCTGCACG|AGGGCAACAA|AAAACCCGGC|ATTTCTGCCG|GGTTTCTGTA|TCCAATCCGT|120|
|AATGGATTAG|AACGAACGCT|GGAAGCGAAC|GATACCGCCC|AAGCATTGT|CTTCAGCAAC|180|
|GGTGTTCTTC|CACTCGCCAC|CAAACTTGGT|GTAGGAAACT|TCCGGCGTAA|CGGTGAAGCC|240|
|AGGAACCAGT|TCGTAAGCAA|CGTTAGCCGT|AACTGCCGTC|TTGCCCCAGT|CGTCATGCGC|300|
|AGCCTGCAGG|TTGAAGGCAG|CCTTCTGCGT|AGCCTGATAC|TTCAGACCAC|CCCAGACAGC|360|
|CCAATCGCCG|CCCCACTGAC|CGTAGTTCTG|GTTCGGCGTC|GCTGCGGACG|AATATGCGCC|420|
|CTGCAGCCAT|ACCGAGAACC|GGTCGGTGAT|GTTGACGTCG|CCACGAACCT|TTGTAGCCCA|480|
|TTCTTCGATG|ACCGAGTCAT|AGGCAACAAC|ACCAGCGATC|GAACCCCAGC|CGCCAGCATA|540|
|TTTCAGGCCG|CCAACAACGT|GCGGCATGTA|ACCGTCGATC|GTGTAATCGT|TGTCAACGTC|600|
|TTCGCCACCC|TGTTCGAGAG|CGATCACAGC|CGAGAAGCCG|TTTCCGCCGG|TGAAGGTGTA|660|
|GGCGATCTTG|CCGGTGCGGT|AGGAGCCAGC|CGAGATCACG|TCATCGTTGA|TGATATCACC|720|
|GAGGTAACCG|GTGAAGGTAT|GGAATTCGGA|TTCGTCGATA|CCAACCTTGA|ACCACCAAG|780|
|CGTGATATAT|GCAAACTGCA|GATCGGTGCC|GGTGCTTACG|CTGCCATCAG|CGACATCACG|840|
|ATCATCGCTG|AAATCGCCGT|ATTGGCCATC|ATGACGTGAA|TTGTTGCTGG|TGTAGTTGAA|900|
|GCGCAGCGTA|GTATAGGTGC|CGAGTGTGCC|GAGTTCGGTT|TCCGAATTCG|TGTTGAACAT|960|
|GGAGTGCAAA|ACGAGCACCT|TGTCCCAGCC|TTTACGATCC|GAGCCGGTAT|AAACGTCGTC|1020|
|GCCGCCCTTT|ACGTCGTAAC|GGACGTAGCC|GCTGATGCGC|AGGCAGGTTT|CGGTGCCCGG|1080|
|AATGTAGAAG|TAGCCAGCGC|CATAAGCGTC|GCAAACGCGG|ACATATTCAA|CGGCTTCGGG|1140|
|CTCTGGCGCG|ACGATTGCGT|CGGCAGCTTG|AGCGCCGGAA|GCTGCAACCA|GAGCTGCAGC|1200|
|GGAGCCAAGG|AGAAGGCTCT|TGATGTTCAT|TTCTGACCTC|CAGTCAAAGT|TAAAAATGGG|1260|
|TCTGGGCATT|CTGATTTGGC|TGAAGGACAA|CCTGTCCCCA|TCCCTAATT|GAAAAAGTCG|1320|
|CCCCGAAGCG|CTCCTTCTTC|TGAAAGTGAA|GATACTCGCC|CATTTATTCG|TTTCAACATC|1380|
|GAATATGTTC|TCACAACCTT|TACGGTGCTG|CTATGAAGGG|CAGTTATTGC|AGAAATGACA|1440|
|CGAAATTACC|TGCTTTAGCT|CGGCGGATTC|ATGCTTTATT|AACATAAGTG|AACGCGAATT|1500|
|AACCGATGTT|AACGTTTGAA|AATGCAAGTT|TTTAGGATC|GCCTGCCGAA|TAAAGCCGCG|1560|
|AATCTTTCGT|CGAAACAGCC|CTTAACGGAA|TATGTCGGCA|AGGTGGCAAG|AATCGTCTGA|1620|

-continued

| | | | | | |
|---|---|---|---|---|---|
| ACGGAGAGCA | GAAACCTCGA | ATCCGTTTCA | TTTAATAAGG | GCAAGTGCGT | GCCGGTGCTA | 1680 |
| AATTGTGGGC | CTTTTTAAGC | GCGCCATATA | TATAAAGAGA | ATAATCCGCA | GGAAATTTTA | 1740 |
| CCAGTTAATG | CGTAAATCGC | TTGAAATGCC | CAGGCGTACC | GGTTATCTCG | CCTTTACCGG | 1800 |
| AGAGGTGGCC | GAGTGGTCGA | AGGCGCTCCC | CTGCTAAGGG | AGTAGACCTC | AAAAGGGTCT | 1860 |
| CGTGGGTTCG | AATCCCATCC | TCTCCGCCAG | TTTTTCCAAT | ATCCCAGCAA | ATCTTTATGT | 1920 |
| GTTCGACGCG | CTTGATTTCA | TACGGAATCG | GCTTTTACCC | CTCGCGCACT | GAATCTCTGT | 1980 |
| TTTTCCAGGC | TACGAATCCA | GAAAACAAGC | AAGCCATTGA | TAAGTAATGG | CTATTCAAAA | 2040 |
| TTCTGGCAAT | TCTTGACTGG | AGGTCAGAAA | TGAACATCAA | GAGCCTTCTC | CTTGGCTCCG | 2100 |
| CTGCAGCTCT | GGTTGCAGCT | TCCGGCGCTC | AAGCTGCCGA | CGCAATCGTC | GCGCCAGAGC | 2160 |
| CCGAAGCCGT | TGAATATGTC | CGCGTTTGCG | ACGCTTATGG | CGCTGGCTAC | TTCTACATTC | 2220 |
| CGGGCACCGA | AACCTGCCTG | CGCATCAGCG | GCTACGTCCG | TTACGACGTA | AAGGGCGGCG | 2280 |
| ACGACGTTTA | TACCGGCTCG | GATCGTAAAG | GCTGGGACAA | GGGTGCTCGT | TTTGCACTCA | 2340 |
| TGTTCAACAC | GAATTCGGAA | ACCGAACTCG | GCACACTCGG | CACCTATACT | CAGCTGCGCT | 2400 |
| TCAACTACAC | CAGCAACAAT | TCACGTCATG | ATGGCCAATA | CGGCGATTTC | AGCGATGATC | 2460 |
| GTGATGTCGC | TGATGGCAGC | GTAAGCACCG | GCACCGATCT | GCAGTTTGCA | TATATCACGC | 2520 |
| TTGGTGGTTT | CAAGGTTGGT | ATCGACGAAT | CCGAATTCCA | TACCTTCACC | GGTTACCTCG | 2580 |
| GTGATATCAT | CAACGATGAC | GTGATCTCGG | CTGGCTCCTA | CCGCACCGGC | AAGATCGCCT | 2640 |
| ACACCTTCAC | CGGCGGAAAC | GGCTTCTCGG | CTGTGATCGC | TCTCGAACAG | GGTGGCGAAG | 2700 |
| ACGTTGACAA | CGATTACACG | ATCGACGGTT | ACATGCCGCA | CGTTGTTGGC | GGCCTGAAAT | 2760 |
| ATGCTGGCGG | CTGGGGTTCG | ATCGCTGGTG | TTGTTGCCTA | TGACTCGGTC | ATCGAAGAAT | 2820 |
| GGGCTACAAA | GGTTCGTGGC | GACGTCAACA | TCACCGACCG | GTTCTCGGTA | TGGCTGCAGG | 2880 |
| GCGCATATTC | GTCCGCAGCG | ACGCCGAACC | AGAACTACGG | TCAGTGGGGC | GGCGATTGGG | 2940 |
| CTGTCTGGGG | TGGTGCAAAG | TTCATTGCCA | CCGAAAAGGC | AACCTTCAAT | CTGCAGGCTG | 3000 |
| CGCATGACGA | CTGGGGCAAG | ACCGCAGTTA | CCGCCAACGT | CGCTTATCAG | CTCGTTCCCG | 3060 |
| GATTCACCAT | TACGCCGGAA | GTTTCCTACA | CCAAATTTGG | TGGCGAGTAG | AAAGACACCG | 3120 |
| TTGCTGAAGA | CAATGCCTGG | GGCGGTATCG | TTCGTTTCCA | GCGCTCGTTC | TAATCAGATC | 3180 |
| GACGTTAAGC | ATAGGGCGCC | AACGGTTTCC | CGTTGGCGCC | GGTTCATTTG | AAACAGCGTT | 3240 |
| CACGAAAGCG | TGAGAATCGA | TTCTTCCGGA | ATGGGGATTC | CAGGCGGATC | GACAATTGAG | 3300 |
| GGAATTGCGG | GGACGACAAA | AAGCTGGGGG | CAACCGGGGG | GTCTTGTAAA | GGATTGAGCC | 3360 |
| A | | | | | | 3361 |

( 2 ) INFORMATION FOR SEQ ID NO:7:

( i ) SEQUENCE CHARACTERISTICS:
        ( A ) LENGTH: 3345 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Brucella melitensis
        ( B ) STRAIN: biovar 1

( x i ) SEQUENCE DESCRIPTION: SEQ ID NO:7:

```
AGGCGATCTT CCGCGACCCC TGTAGAAAGA CTGCGGTCAG CATAAAAAGC AAGCATCTGA 60
TGCTGCACGA GGGCAACAAA AAACCCGGCA TTTCTGCCGG GTTTCTGTAT CCAATCCGTA 120
ATGGATTAGA ACGAACGCTG GAAGCGAACG ATACCGCCCC AAGCATTGTC TTCAGCAACA 180
```

| | | | | | |
|---|---|---|---|---|---|
| GTGTTCTTCC | ACTCGCCACC | AAACTTGGTG | TAGGAAACTT | CCGGCGTAAC | GGTGAAGCCA | 240 |
| GGAACCAGTT | CGTAAGCAAC | GTTAGCCGTA | ACTGCCGTCT | TGCCCCAGTC | GTCATGCGCA | 300 |
| GCCTGCAGGT | TGAAGGCAGC | CTTCTGCGTA | GCCTGATACT | TCAGACCACC | CCAGACAGCC | 360 |
| CAATCGCCGC | CCCACTGGCC | GTAGTTCTGA | TCCGGCGTAG | CAGCGGACGA | ATATGCGCCC | 420 |
| TGCAACCAAA | CCGAGAACTG | GTCGGTGATG | TTGACGTCGC | CACGAACCTT | GGCAGCCCAT | 480 |
| TCTTCGATGA | CCGAGTCATA | GGCAACAACA | CCAGCGATCG | AACCCCAGCC | GCCAGCATAC | 540 |
| TTCAGGCCGC | CAACAACGTC | AGGCATGTAG | CCGTCGATGT | GGTAGTTGGT | CGTGCCAGTG | 600 |
| TAACCACCGT | CGTTGTCGCC | ACCCTGTTCG | AGAGCGATCA | CAGCCGAGAA | GCCGTTTCCG | 660 |
| CCAGTGAAGG | TGTACGAGAT | CTTGCCGGTG | CGGTAGGAGC | CAGCCGAGAT | CACGTCATCG | 720 |
| TTGATGACAT | CGCCGAGGTA | ACCGGTGAAG | GTATGGAATT | CCGATTCATC | GATACCAACG | 780 |
| CGCAGACCAC | CGAGCTGGAT | ATACGCGAAC | TCCATGACGG | TGCCGCTGCT | GGTTTCATTA | 840 |
| CCATATTTAC | CATCTACGCC | CGAATTGTTC | GCAGCATAGT | TGAAGCGCAG | TTCGGTGAAG | 900 |
| GTCTTGAGGG | TGCCGAGTTC | GGTTTCCGAA | CCGGTGGAAA | CGCGGAGTGC | GAAACGAGCG | 960 |
| CCCTTGTCCC | AGCCATTGCG | GTCGGTACCG | GAGTAAACGT | CATCGCCGCC | CTTTACGTCG | 1020 |
| TAACGGACGT | AACCATGGAC | GCGCAGGCAG | GTTCGGTGC | CCGGAATGTA | GAAGTAGCCA | 1080 |
| GCGCCGTAAG | CGTCGCAAAC | GCGGACATAT | TCAACGGCTT | CGGGCTCTGG | CGCGACGATT | 1140 |
| GCGTCGGCAG | CCTGAGCGCC | GGAAGCTGCA | ACCAGAGCTG | CAGCGGAGCC | AAGGAGAAGG | 1200 |
| CTCTTGATGT | TCATTTCTGA | CCTCCAGTCA | AGTTAAAAA | TGGGTCTGGG | CATTCTGATT | 1260 |
| TGGCTGAAGG | ACAACCTGTC | CCCATCCCCT | AATTGAAAAA | GTCGCCCCGA | AGCGCTCCTT | 1320 |
| CTTCTGAAAG | TGAAGATACT | CGCCCATTTA | TTCGTTTCAA | CATCGAATAT | GTTCTCACAA | 1380 |
| CCTTTACGGT | GCTGCTATGA | AGGGCAGTTA | TTGCAGAAAT | GACACGAAAT | TACCTGCTTT | 1440 |
| AGCTCGGCGG | ATTCATGCTT | TATTAACATA | AGTGAACGCG | AATTAACCGA | TGTTAACGTT | 1500 |
| TGAAAATGCA | AGTTTTTTAG | GATCGCCTGC | CGAATAAAGC | CGCGGATCTT | TCGTCGAAAC | 1560 |
| AGCCCTTAAC | GGAATATGTC | GGCAAGGTGG | CAAGAATCGT | CTGAACGGAG | AGCAGAAACC | 1620 |
| TCGAATCCGT | TTCATTTAAT | AAGGGCAAGT | GCGTGCCGGT | GCTAAATTGT | GGGCCTTTTT | 1680 |
| AAGCGCGCCA | TATATATAAA | GAGAATAATC | CGCAGGAAAT | TTTACCAGTT | AATGCGTAAA | 1740 |
| TCGCTTGAAA | TGCCCAGGCG | TACCGGTTAT | CTCGCCTTTA | CCGGAGAGGT | GGCCGAGTGG | 1800 |
| TCGAAGGCGC | TCCCTGCTA | AGGGAGTAGA | CCTCAAAAGG | GTCTCGTGGG | TTCGAATCCC | 1860 |
| ATCCTCTCCG | CCAGTTTTTC | CAATATCCCA | GCAAATCTTT | ATGTGTTCGA | CGCGCTTGAT | 1920 |
| TTCATACGGA | ATCGGCTTTT | ACCCCTCGCG | CACTGAATCT | CTGTTTTTCC | AGGCTACGAA | 1980 |
| TCCAGAAAAC | AAGCAAGCCA | TTGATAAGTA | ATGGCTATTC | AAAATTCTGG | CGATTCTTGA | 2040 |
| CTGGAGGTCA | GAAATGAACA | TCAAGAGCCT | TCTCCTTGGC | TCCGCCGCAG | CTCTGGTTGC | 2100 |
| AGCTTCCGGC | GCTCAGGCTG | CCGACGCAAT | CGTCGCGCCA | GAGCCCGAAG | CCGTTGAATA | 2160 |
| TGTCCGCGTT | TGCGACGCTT | ACGGCGCTGG | CTACTTCTAC | ATTCCGGGCA | CCGAAACCTG | 2220 |
| CCTGCGCGTC | CATGGTTACG | TCCGTTACGA | CGTAAAGGGC | GGCGATGACG | TTTACTCCGG | 2280 |
| TACCGACCGC | AATGGCTGGG | ACAAGGGCGC | TCGTTTCGCA | CTCATGTTCA | ACACGAATTC | 2340 |
| GGAAACCGAA | CTCGGCACAC | TCGGCACCTA | TACTCAGCTG | CGCTTCAACT | ACACCAGCAA | 2400 |
| CAATTCACGT | CATGATGGCC | AATACGGCGA | TTTCAGCGAT | GATCGTGATG | TCGCTGATGG | 2460 |
| CGGCGTAAGC | ACCGGCACCG | ATCTGCAGTT | TGCATATATC | ACGCTTGGTG | GTTTCAAGGT | 2520 |
| TGGTATCGAC | GAATCCGAAT | TCCATACCTT | CACCGGTTAC | CTCGGTGATG | TCATCAACGA | 2580 |
| TGATGTCGTC | GCTGCTGGCT | CCTACCGCAC | CGGCAAGATC | GCCTACACCT | TCACCGGCGG | 2640 |

| | | | | | |
|---|---|---|---|---|---|
| AAACGGCTTC | TCGGCTGTGA | TCGCTCTCGA | ACAGGGTGGC | GAAGACGTTG | ACAACGATTA | 2700
| CACGATCGAC | GGTTACATGC | CGCACGTTGT | TGGCGGCCTG | AAATATGCTG | GCGGCTGGGG | 2760
| TTCGATCGCT | GGTGTTGTTG | CCTATGACTC | GGTCATCGAA | GAATGGGCTA | CAAAGGTTCG | 2820
| TGGCGACGTC | AACATCACCG | ACCGGTTCTC | GGTATGGCTG | CAGGGCGCAT | ATTCGTCCGC | 2880
| AGCGACGCCG | AACCAGAACT | ACGGTCAGTG | GGGCGGCGAT | TGGGCTGTCT | GGGGTGGTGC | 2940
| AAAGTTCATT | GCCACCGAAA | AGGCAACCTT | CAATCTGCAG | GCTGCGCATG | ACGACTGGGG | 3000
| CAAGACCGCA | GTTACCGCCA | ACGTCGCTTA | TCAGCTCGTT | CCCGGATTCA | CCATTACGCC | 3060
| GGAAGTTTCC | TACACCAAAT | TGGTGGCGA | GTGGAAAGAC | ACCGTTGCTG | AAGACAATGC | 3120
| CTGGGGCGGT | ATCGTTCCTT | TCCAGCGCTC | GTTCTAATCA | GATCGACGTT | AAGCATAGGG | 3180
| CGCCAACGGT | TTCCCGTTGG | CGCCGGTTCA | TTTGAAACAG | CGTTCACGAA | AGCGTGAGAA | 3240
| TCGATTCTTC | CGGAATGGGG | ATTCCAGGCG | GATCGACAAT | TGAGGGAATT | GCGGGGACGA | 3300
| CAAAAAGCTG | GGGGCAACCG | GGGGGTCTTG | TAAAGGATTG | AGCCA | | 3345

( 2 ) INFORMATION FOR SEQ ID NO:8:

( i ) SEQUENCE CHARACTERISTICS:
    ( A ) LENGTH: 3347 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Brucells suis
    ( B ) STRAIN: biovar 1

( x i ) SEQUENCE DESCRIPTION: SEQ ID NO:8:

```
CAGGCGATCT TCCGCGACCC CTGTAGAAAG ACTGCGGTCA GCATAAAAAG CAAGCATCTG     60
ATGCTGCACG AGGGCAACAA AAAACCCGGT ATTTCTGCCG GGTTTCTGTA TCCAATCCGT    120
AATGGATTAG AACGAACGCT GGAAGCGAAC GATACCGCCC CAAGCATTGT CTTCAGCAAC    180
GGTGTTCTTC CACTCGCCAC CAAACTTGGT GTAGGAAACT TCCGGCGTAA CGGTGAAGCC    240
AGGAACCAGT TCGTAAGCAA CGTTAGCCGT AACTGCCGTC TTGCCCCAGT CGTCATGCGC    300
AGCCTGCAGG TTGAAGGCAG CCTTCTGCGT AGCCTGATAC TTCAGACCAC CCCAGACAGC    360
CCAATCGCCG CCCCACTGGC CGTAGTTCTG ATCCGGCGTA GCAGCGGACG AATATGCGCC    420
CTGCAACCAA ACCGAGAACT GGTCGGTGAT GTTGACGTCG CCACGAACCT TGGCAGCCCA    480
TTCTTCGATG ACCGAGTCAT AGGCAACAAC ACCAGCGATC GAACCCCAGC CGCCAGCATA    540
CTTCAGGCCG CCAACAACGT CAGGCATGTA GCCGTCGATG CGGTAGTTGG TCGTGCCAGT    600
GTAACCACCG TCGTTGTCGC CACCCTGTTC GAGAGCGATC ACAGCCGAGA AGCCGTTTCC    660
GCCAGTGAAG GTGTACGAGA TCTTGCCGGT GCGGTAGGAG CCAGCCGAGA TCACGTCATC    720
GTTGATGACA TCGCCGAGGT AACCGGTGAA GGTATGGAAT TCCGATTCAT CGATACCAAC    780
GCGCAGACCA CCGAGCTGGA TATACGCGAA CTCCATGACG GTGCCGCTGC TGGTTTCATT    840
ACCATATTTA CCATCTACGC CCGAATTGTT CGCAGCATAG TTGAAGCGCA GTTCGGTGAA    900
GGTCTTGAGG GTGCCGAGTT CGGTTTCCGA ACCGGTGGAA ACGCGGAGTG CGAAACGAGC    960
GCTCTTGTCC CAGCCATTGC GGTCGGTACC GGAGTAAACG TCATCGCCGC CCTTTACGTC   1020
GTAACGGACG TAACCATGGA CGCGCAGGCA GGTTTCGGTG CCCGGAATGT AGAAGTAGCC   1080
AGCGCCGTAA GCGTCGCAAA CGCGGACATA TTCAACGGCT TCGGGCTCTG GCGCGACGAT   1140
TGCGTCGGCA GCCTGAGCGC CGGAAGCTGC AACCAGAGCT GCAGCGGAGC CAAGGAGAAG   1200
```

```
GCTCTTGATG TTCATTTCTG ACCTCCAGTC AAAGTTAAAA ATGGGTCTGG GCATTCTGAT      1260
TTGGCTGAAG GACAACCTGT CCCCATCCCC TAATTGAAAA AGTCGCCCCG AAGCGCTCCT      1320
TCTTCTGAAA GTGAAGATAC TCGCCCATTT ATTCGTTTCA ACATCGAATA TGTTCTCACA      1380
ACCTTTACGG TGCTGCTATG AAGGGCAGTT GTTGCTGAAA TGACACGAAA TTACCTGCTT      1440
TAGCTCGGCG GATTCATGCT TTATTAACAT AAGTGAACGC GAATTAACCG ATGTTAACGT      1500
TTGAAAATGC AAGTTTTTA GGATCGCCTA CCGAATAAAG CCGCGAATCT TTCGTCGAAA       1560
CAGCCCTTAA CGGAATATGT CGGCAAGGTG GCAAGAATCG TCTGAACGGA GAGCAGAAAC      1620
CTCGAATCCG TTTCATTTAA TAAGGGCAAG TGCGTGCCGG TGCTAAATTG TGGGCCTTTT      1680
TAAGCGCGCT ATATATATAA AGAGAATAAT CCGCAGGAAA TTTTACCAGT TAATGCGTAA      1740
ATCGCTTGAA ATGCCCAGGC GTACCGGTTA TCTCGCCTTT ACCGGAGAGG TGGCCGAGTG      1800
GTCGAAGGCG CTCCCCTGCT AAGGGAGTAG ACCTCAAAAG GGTCTCGTGG GTTCGAATCC      1860
CATCCTCTCC GCCAGTTTTT CCAATATCCC AGCAAATCTT TATGTGTTCG ACGCGCTTGA      1920
TTTCATACGG AATCGGCTTT TACCCCTCGC GCACTGAATC TCTGTTTTTC CAGGCTACGA      1980
ATCCAGAAAA CAAGCAAGCC ATTGATAAGT AATGGCTATT CAAAATTCTG GCGATTCTTG      2040
ACTGGAGGTC AGAAATGAAC ATCAAGAGCC TTCTCCTTGG CTCCGCTGCA GCTCTGGTTG      2100
CAGCTTCCGG CGCTCAGGCT GCCGACGCAA TCGTCGCGCC AGAGCCCGAA GCCGTTGAAT      2160
ATGTCCGCGT TTGCGACGCT TACGGCGCTG GCTACTTCTA CATTCCGGGC ACCGAAACCT      2220
GCCTGCGCGT CCATGGTTAC GTCCGTTACG ACGTAAAGGG CGGCGACGAC GTTTATACCG      2280
GCTCGGATCG TAAAGGCTGG GACAAGGGCG CTCGTTTCGC ACTCATGTTC AACACGAATT      2340
CGGAAACCGA ACTCGGCACA CTCGGCACCT ATACTCAGCT GCGCTTCAAC TACACCAGCA      2400
ACAATTCACG TCATGATGGC CAATACGGCG ATTTCAGCGA TGATCGTGAT GTCGCTGATG      2460
GCGGCGTAAG CACCGGCACC GATCTGCAGT TTGCATATAT CACGCTTGGT GGTTTCAAGG      2520
TTGGTATCGA CGAATCCGAA TTCCATACCT TCACCGGTTA CCTCGGTGAT GTCATCAACG      2580
ATGATGTCGT CGCTGCTGGC TCCTACCGCA CCGGCAAGAT CGCCTACACC TTCACCGGCG      2640
GAAACGGCTT CTCGGCTGTG ATCGCTCTCG AACAGGGTGG CGAAGACGTT GACAACGATT      2700
ACACGATCGA CGGTTACATG CCGCACGTTG TTGGCGGCCT GAAATATGCT GGCGGCTGGG      2760
GTTCGATCGC TGGTGCTGTT GCCTATGACC CGGTCATCGA AGAATGGGCT ACAAAGGTTC      2820
GTGGCGACGT CAACATCACC GACCGGTTCT CGGTATGGCT GCAGGGCGCA TATTCGTCCG      2880
CAGCGACGCC GAACCAGAAC TACGGTCAGT GGGGCGGCGA TTGGGCTGTC TGGGGTGGTG      2940
CAAAGTTCAT TGCCACCGAA AAGGTAACCT TCAATCTGCA GGCTGCGCAT GACGACTGGG      3000
GCAAGACCGC AGTTACCGCC AACGTCGCTT ATCAGCTCGT TCCCGGATTC ACCATTACGC      3060
CGGAAGTTTC CTACACCAAA TTTGGTGGCG AGTGGAAAGA CACCGTTGCT GAAGACAATG      3120
CCTGGGGCGG TATCGTTCGC TTCCAGCGCT CGTTCTAATC AGATCGACGT TAAGCATAGG      3180
GCGCCAACGG TTTCCCGTTG GCGCCGGTTC ATTTGAAACA GCGTTCACGA AAGCGTGAGA      3240
ATCGATTCTT CCGGAATGGG GATTCCAGGC GGATCGACAA TTGAGGGAAT TGCGGGACG      3300
ACAAAAAGCT GGGGGCAACC GGGGGGTCTT GTAAAGGATT GAGCCAC                    3347
```

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

CGCGAACTCC ATGACGGTGC CGC                    23

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

CCTTGGCTCC GCTGCAGCTC TGGT                    24

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

CAGGCGATCT TCCGCGACCC C                    21

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GGGGATGGGG ACAGGTTGTC C                    21

( 2 ) INFORMATION FOR SEQ ID NO:13:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

TGGGTCTGGG CATTCTGATT TGGCTG                    26

( 2 ) INFORMATION FOR SEQ ID NO:14:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

TCGCCAGAAT TTTGAATAGC CATTAC                    26

( 2 ) INFORMATION FOR SEQ ID NO:15:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:15:

CCTTGGCTCC GCTGCAGCTC TGGT 24

( 2 ) INFORMATION FOR SEQ ID NO:16:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

CGTTGTCAAC GTCTTCGCCA CCC 23

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

CCGGCGGCCA ACGGGAAACC G 21

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

CGGCTTTACC CCTCGCGCAC 20

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

TGGCTCAATC CTTTACAA 18

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

TCGTGATGTC GCTGATGG                                                                                            1 8

( 2 ) INFORMATION FOR SEQ ID NO:21:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:21:

ATGTCGTCGC TGCTGGCTCC                                                                                          2 0

( 2 ) INFORMATION FOR SEQ ID NO:22:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:22:

ATGTCGTCGC TGATGGCTCC                                                                                          2 0

( 2 ) INFORMATION FOR SEQ ID NO:23:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:23:

ACGTGATCTC GGCTGGCTCC                                                                                          2 0

( 2 ) INFORMATION FOR SEQ ID NO:24:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:24:

TGTTGTTGCC TATGACTCGG                                                                                          2 0

( 2 ) INFORMATION FOR SEQ ID NO:25:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:25:

TGCTGTTGCC TATGACCCGG                                                                                          2 0

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

CCCCGAAAAG GCAACCTTCA 20

( 2 ) INFORMATION FOR SEQ ID NO:27:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

CACCGAAAAG GCAACCTTCA 20

( 2 ) INFORMATION FOR SEQ ID NO:28:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

CACCGAAAAG GTAACCTTCA 20

( 2 ) INFORMATION FOR SEQ ID NO:29:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

AGACCGCAGT TACCGCCAAC 20

( 2 ) INFORMATION FOR SEQ ID NO:30:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

AGACGGCAGT TACGGCTAAC 20

( 2 ) INFORMATION FOR SEQ ID NO:31:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

GTCGCTTATC AGCTCGTTCC 20

( 2 ) INFORMATION FOR SEQ ID NO:32:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: cDNA ( x i ) SEQUENCE DESCRIPTION: SEQ ID NO:32:

GTTGCTTACG AACTGGTTCC 20